(12) United States Patent
Melemedjian

(10) Patent No.: US 12,128,062 B2
(45) Date of Patent: Oct. 29, 2024

(54) METHODS FOR TARGETING PAIN DIRECTED AT METABOLIC PATHWAYS

(71) Applicant: Ohannes Kevork Melemedjian, Baltimore, MD (US)

(72) Inventor: Ohannes Kevork Melemedjian, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 899 days.

(21) Appl. No.: 17/258,544

(22) PCT Filed: Aug. 14, 2019

(86) PCT No.: PCT/US2019/046475
§ 371 (c)(1),
(2) Date: Jan. 7, 2021

(87) PCT Pub. No.: WO2020/037030
PCT Pub. Date: Feb. 20, 2020

(65) Prior Publication Data
US 2021/0161944 A1   Jun. 3, 2021

Related U.S. Application Data

(60) Provisional application No. 62/718,468, filed on Aug. 14, 2018.

(51) Int. Cl.
| | | |
|---|---|---|
| *C12N 15/11* | (2006.01) | |
| *A61K 31/16* | (2006.01) | |
| *A61K 31/19* | (2006.01) | |
| *A61K 31/7004* | (2006.01) | |
| *A61K 31/7105* | (2006.01) | |
| *A61K 47/54* | (2017.01) | |
| *C12N 15/113* | (2010.01) | |

(52) U.S. Cl.
CPC .......... *A61K 31/7105* (2013.01); *A61K 31/16* (2013.01); *A61K 31/19* (2013.01); *A61K 31/7004* (2013.01); *A61K 47/543* (2017.08); *A61K 47/549* (2017.08); *C12N 15/1138* (2013.01); *C12N 2310/11* (2013.01); *C12N 2310/346* (2013.01)

(58) Field of Classification Search
CPC ................. C12N 15/1138; C12N 2310/11
See application file for complete search history.

(56) References Cited

U.S. PATENT DOCUMENTS

2004/0126368 A1  7/2004  Miller
2008/0153768 A1  6/2008  Dorn et al.

FOREIGN PATENT DOCUMENTS

WO   2017/011766   1/2017

OTHER PUBLICATIONS

International Search Report and Written Opinion of the International Searching Authority, issued Nov. 18, 2019 in corresponding International Patent Application No. PCT/US19/46475.
Gegelashvili et al., "High-affinity glutamate transporters in chronic pain: an emerging therapeutic target", Journal of Neurochemistry, 131: 712-730 (2014).
Genbank Submission AK055630, *Homo sapiens* cDNA FLJ3 1068 fis, clone HSYRA2001232, highly similar to neutral amino acid transporter B; Jan. 9, 2008. Retrieved from the internet (URL: https://www.ncbi.nlm.nih.gov/nuccore/AK055630) on Oct. 18, 2019.

*Primary Examiner* — Ekaterina Poliakova-Georgantas
(74) *Attorney, Agent, or Firm* — Wenderoth, Lind & Ponack, L.L.P.

(57) ABSTRACT

Methods of alleviating or prophylactically blocking pain through the alteration of certain metabolic pathways in a subject experiencing pain or expecting to experience pain are disclosed. In particular, methods of increasing the amount of the neutral amino acid transporter ASCT2 in neurons are disclosed. Increased glutamine uptake by neurons leads to reduced extrusion of lactate and protons into the extracellular space and by extension, reduced sensitization of the neurons. Reduced sensitization of the neurons lessens the feeling of pain in the subject.

17 Claims, 5 Drawing Sheets

Specification includes a Sequence Listing.

METHODS FOR TARGETING PAIN DIRECTED AT METABOLIC PATHWAYS

CROSS-REFERENCE TO RELATED APPLICATIONS

The present application claims benefit of U.S. Provisional Application No. 62/718,468, filed Aug. 14, 2018.

SEQUENCE LISTING

A sequence listing in electronic (ASCII text file) format is filed with this application and incorporated herein by reference. The ASCII text file is named "2019_1311A_ST25.txt"; the file was created on Aug. 14, 2019; the size of the file is 11 KB.

BACKGROUND OF INVENTION

Currently available means for treating pain, whether acute or chronic, are inadequate and, in some cases, hazardous to the long-term health of an individual. For example, opioids are the mainstay treatment for a variety of chronic pain conditions. Opioids are efficacious in providing pain relief acutely, however persistent use of opioids can induce delayed hypersensitivity due to a reduction in their analgesic efficacy and development of tolerance. Moreover, in a pre-clinical study administration of fentanyl exaggerated postoperative pain in rats [26]. Apart from serious side effects, opioids have severe potential for abuse liability. Opioid-naïve patients undergoing surgery are at an increased risk for subsequent chronic opioid use [27]. Moreover, around 80% of heroin addicts report using prescription opioids prior to heroin [28-30]. Crucially, according to the U.S. Centers for Disease Control and Prevention, the United States is in the midst of an epidemic for opioid-related overdose deaths [31]. The estimated cost of this epidemic is around $80 billion [32]. Thus, there is an urgent need to develop non-addictive strategies to treat post-surgical pain.

As another example, chemotherapy-induced painful peripheral neuropathy (CIPN) is the most prevalent toxicity associated with widely used anti-cancer drugs, which include taxanes, platinum-based drugs, vinca alkaloids and proteasome inhibitors. This adverse effect can be severe enough for patients to either reduce the dosage of anti-cancer treatment or stop the treatment altogether. CIPN can even persist in cancer survivors, thus negatively impacting their quality of life [55-57]. Currently, treatment options for CIPN are vastly inadequate which warrants a better understanding of the mechanisms that underpin CIPN and new treatment options.

Uncovering new means for treating pain are critical for the development of novel therapeutic strategies. The present invention is directed to these and other important goals.

BRIEF SUMMARY OF INVENTION

The present invention generally relates to methods of alleviating or blocking pain through the alteration of certain metabolic pathways in a subject experiencing pain or a subject expected to develop a chronic pain condition. In particular, the methods of the present invention are based on increasing the amount of the neutral amino acid transporter, ASCT2 (gene name: SLC1A5), in neurons. As discussed below, increased glutamine uptake by neurons can lead to reduced extrusion of lactate and protons into the extracellular space and by extension, reduced sensitization of the neurons. Reduced sensitization of the neurons lessens the feeling of pain in a subject.

In a first embodiment, the invention is directed to methods of alleviating pain in a subject, comprising administering a therapeutically effective amount of ASCT2-targeted teRNA (translation enhancing RNA) to a subject in need thereof. In preferred aspects of this embodiment, the subject is experiencing pain at the time the ASCT2-targeted teRNA is administered. Thus, the administering is a treatment for pain in the subject.

In a second embodiment, the invention is directed to methods of prophylactically blocking pain in a subject, comprising administering a therapeutically effective amount of ASCT2-targeted teRNA to a subject in need thereof. In preferred aspects of this embodiment, the subject is not experiencing pain at the time the ASCT2-targeted teRNA is administered. Thus, the administering is a prophylaxis before pain develops in the subject.

In each of these embodiments, the ASCT2-targeted teRNA is a RNA molecule that binds with specificity to the upstream Open Reading Frame (uORF) of ASCT2 mRNA and interferes with ribosomal interaction with the uORF. In certain aspects, the RNA molecule may range in size from about 10 to 40 nucleotides in length.

Suitable ASCT2-targeted teRNAs for use in the methods of the invention include, but are not limited to, the following teRNAs: 5'-CAUGCCUCAGCCCGGCAGGG-3' (SEQ ID NO:4); 5'-CAUGCCUCAGCCCGGCAG-3' (SEQ ID NO:5); 5'-CAUGCCUCAGCCCGGC-3' (SEQ ID NO:6); 5'-CAUUGUCUGAGAGGCUGGGU-3' (SEQ ID NO:7); 5'-CAUUGUCUGAGAGGCUGG-3' (SEQ ID NO:8); 5'-CAUUGUCUGAGAGGCU-3' (SEQ ID NO:9); 5'-CAUUGUGGGUUCGGGGUGAG-3' (SEQ ID NO:10); 5'-CAUUGUGGGUUCGGGGUG-3' (SEQ ID NO:11); 5'-CAUUGUGGGUUCGGGG-3' (SEQ ID NO:12); 5'-CAUGCAGCAAACUUAAUACC-3' (SEQ ID NO:13); 5'-CAUGCAGCAAACUUAAUA-3' (SEQ ID NO:14); 5'-CAUGCAGCAAACUUAA-3' (SEQ ID NO:15); 5'-CAUUGUCUGAGAGGCUGGGU-3' (SEQ ID NO:16); 5'-CAUUGUCUGAGAGGCUGG-3' (SEQ ID NO:17); 5'-CAUUGUCUGAGAGGCU-3' (SEQ ID NO:18); 5'-CAUGCCUCAGCCCGGCAGGG-3' (SEQ ID NO:19); 5'-CAUGCCUCAGCCCGGCAG-3' (SEQ ID NO:20); 5'-CAUGCCUCAGCCCGGC-3' (SEQ ID NO:21); 5'-CAUUGUGGGUUCGGGGUGAG-3' (SEQ ID NO:22); 5'-CAUUGUGGGUUCGGGGUG-3' (SEQ ID NO:23); 5'-CAUUGUGGGUUCGGGG-3' (SEQ ID NO:24); 5'-CAUGGAGAAACCCCAUCUCU-3' (SEQ ID NO:25); 5'-CAUGGAGAAACCCCAUCU-3' (SEQ ID NO:26); 5'-CAUGGAGAAACCCCAU-3' (SEQ ID NO:27); 5'-CAUUUGUGUUUUGAAAAGAU-3' (SEQ ID NO:28); 5'-CAUUUGUGUUUUGAAAAG-3' (SEQ ID NO:29); 5'-CAUUUGUGUUUUGAAA-3' (SEQ ID NO:30); 5'-CAUGGCAGGGCUCUGGGUAC-3' (SEQ ID NO:31); 5'-CAUGGCAGGGCUCUGGGU-3' (SEQ ID NO:32); 5'-CAUGGCAGGGCUCUGG-3' (SEQ ID NO:33); 5'-CAUAGACUGUAGCAAGGAGA-3' (SEQ ID NO:34); 5'-CAUAGACUGUAGCAAGGA-3' (SEQ ID NO:35); 5'-CAUAGACUGUAGCAAG-3' (SEQ ID NO:36); 5'-CAUAAUCUACUGUGGCUAGA-3' (SEQ ID NO:37); 5'-CAUAAUCUACUGUGGCUA-3' (SEQ ID NO:38); 5'-CAUAAUCUACUGUGGC-3' (SEQ ID NO:39); 5'-CAUUCAAAGAAGAGCCAUAA-3' (SEQ ID NO:40); 5'-CAUUCAAAGAAGAGCCAU-3' (SEQ ID NO:41); 5'-CAUUCAAAGAAGAGCC-3' (SEQ ID NO:42); 5'-CAUCUGAGCUGAGACCUGGA-3' (SEQ ID NO:43);

5'-CAUCUGAGCUGAGACCUG-3' (SEQ ID NO:44); 5'-CAUCUGAGCUGAGACC-3' (SEQ ID NO:45).

Suitable ASCT2-targeted teRNAs for use in the methods of the invention also include, but are not limited to, sequence variants of the teRNAs set forth in SEQ ID NOs:4-45 having at least 90% sequence identity over their entire length to a teRNAs set forth in one of SEQ ID NOs:4-45 and having the same activity as the teRNA upon which they are based.

The ASCT2-targeted teRNA may contain one or more of the following chemical modifications and/or nucleotide analogs: phosphodiester backbone; phosphorothioate backbone; 2-aminopurine; 2,6-diaminopurine; 5-bromo-deoxyuridine; deoxyuridine; inverted dideoxy-T incorporated at the 3'- and/or 5'-end; 5-methyl deoxycytidine; deoxyInosine; super T (5-hydroxybutynl-2'-deoxyuridine); super G (8-aza-7-deazaguanosine); locked nucleic acids; 5-nitroindole; 2'-O-methyl RNA; hydroxymethyl dC; iso-dC; iso-dG; fluoro C, U, A or G; one or more 2'-O-methoxy-ethyl bases.

Alternatively, or in addition, the ASCT2-targeted teRNA may be conjugated with N-acetylgalactosamine (GalNAc) or combined with a lipid or polymer.

The ASCT2-targeted teRNA may be formulated as a pharmaceutical composition comprising one or more ASCT2-targeted teRNA and a pharmaceutically acceptable carrier, diluent or excipient.

The ASCT2-targeted teRNA may be administered to the subject via means including, but not limited to, intrathecal administration. In certain aspects of the invention, intrathecal administration is direct administration to trigeminal and/or dorsal root ganglia.

In the methods of alleviating pain in a subject in need thereof, the subject may be experiencing acute pain or chronic pain, of any duration or intensity. The pain may be, but is not limited to, one or more of the following types of pain and/or pain associated with one or more of the following conditions or diseases: cancer pain, CIPN, AIDS-related pain, ankylosing spondylitis, arachnoiditis, arthritis, arthrofibrosis, ataxic cerebral palsy, autoimmune atrophic gastritis, autoimmune diseases, avascular necrosis, back pain, breakthrough pain, burning mouth syndrome, bursitis, CARDASIL syndrome, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pancreatitis, coccyx, collapsed lung (pneumothorax), complex regional pain syndrome, corneal neuropathic pain, Crohn's disease, degenerative disc disease, Dercum's disease, dermatomyositis, diabetic peripheral neuropathy, dystonia, Rhlers-Danlos syndrome, endometriosis, eosinophilia-myalgia syndrome, erythromelalgia, failed back surgery syndrome, fibromyalgia, gout, headaches, herniated disc, hydrocephalus, intercostal neuraligia, interstitial cystitis, irritable bowel syndrome, juvenile dermatositis, loin pain-haematuria syndrome, lupus, lyme disease, medullary sponge kidney, meralgia paresthetica, mesothelioma, migraine, mitochondrial disorders, multiple sclerosis, musculoskeletal pain, myofascial pain, myositis, neuropathic pain, occipital neuralgia, osteoarthritis, Paget's disease, parsonage turner syndrome, pelvic pain, peripheral neuropathy, phantom limb pain, pinched nerve, polycystic kidney disease, polymyalgia rhuematica, polymyositis, porphyria, post-herniorraphy pain syndrome, post-mastectomy pain syndrome, post-stroke pain, post-thorocotomy pain syndrome, post-herpetic neuralgia (shingles), post-polio syndrome, primary lateral sclerosis, psoriatic arthritis, pudendal neuralgia, radiculopathy, Raynaud's disease, rheumatoid arthritis, sacroiliac joint dysfunction, sarcoidosis, Scheuemann's kyphosis disease, sciatica, scoliosis, sickle cell, Sjogren's syndrome, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, temporomandibular joint disorder, transverse myelitis, trigeminal neuralgia, ulcerative colitis, vascular pain, vulvodynia and whiplash.

In the methods of prophylactically blocking pain in a subject in need thereof, the subject is expecting to experience pain in the near future, such as, but not limited to, a subject that will undergo a surgical procedure or medical treatment that is expected to cause pain. The pain may be, but is not limited to, one or more of the following types of pain and/or pain associated with one or more of the following conditions or diseases: cancer pain, CIPN, AIDS-related pain, ankylosing spondylitis, arachnoiditis, arthritis, arthrofibrosis, ataxic cerebral palsy, autoimmune atrophic gastritis, autoimmune diseases, avascular necrosis, back pain, breakthrough pain, burning mouth syndrome, bursitis, CARDASIL syndrome, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pancreatitis, coccyx, collapsed lung (pneumothorax), complex regional pain syndrome, corneal neuropathic pain, Crohn's disease, degenerative disc disease, Dercum's disease, dermatomyositis, diabetic peripheral neuropathy, dystonia, Rhlers-Danlos syndrome, endometriosis, eosinophilia-myalgia syndrome, erythromelalgia, failed back surgery syndrome, fibromyalgia, gout, headaches, herniated disc, hydrocephalus, intercostal neuraligia, interstitial cystitis, irritable bowel syndrome, juvenile dermatositis, loin pain-haematuria syndrome, lupus, lyme disease, medullary sponge kidney, meralgia paresthetica, mesothelioma, migraine, mitochondrial disorders, multiple sclerosis, musculoskeletal pain, myofascial pain, myositis, neuropathic pain, occipital neuralgia, osteoarthritis, Paget's disease, parsonage turner syndrome, pelvic pain, peripheral neuropathy, phantom limb pain, pinched nerve, polycystic kidney disease, polymyalgia rhuematica, polymyositis, porphyria, post-herniorraphy pain syndrome, post-mastectomy pain syndrome, post-stroke pain, post-thorocotomy pain syndrome, post-herpetic neuralgia (shingles), post-polio syndrome, primary lateral sclerosis, psoriatic arthritis, pudendal neuralgia, radiculopathy, Raynaud's disease, rheumatoid arthritis, sacroiliac joint dysfunction, sarcoidosis, Scheuemann's kyphosis disease, sciatica, scoliosis, sickle cell, Sjogren's syndrome, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, temporomandibular joint disorder, transverse myelitis, trigeminal neuralgia, ulcerative colitis, vascular pain, vulvodynia and whiplash.

In both embodiments, the invention may further comprise administering one or more therapeutically effective agents to the subject. A therapeutically effective agent is one that counteracts the metabolic changes in a sensory neuron. Suitable therapeutically effective agents include, but are not limited to, dichloroacetate (DCA), oxamate and 2-deoxy-d-glucose (2DG). Thus, the invention includes methods of alleviating or prophylactically blocking pain in a subject, comprising administering (i) a therapeutically effective amount of ASCT2-targeted teRNA and (ii) a therapeutically effective amount of one or more of DCA, oxamate and 2DG to a subject in need thereof. In certain aspects, the combination of teRNA with one or more of DCA, oxamate and 2DG is a synergistic combination that is sufficient to alleviate or prophylactically block a variety of chronic pain states. The ASCT2-targeted teRNA and the one or more of DCA, oxamate and 2DG may be administered to the subject sequentially or concurrently, and in any order.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of the invention.

BRIEF DESCRIPTION OF DRAWINGS

FIG. 2A) Paw incision of mice caused hypersensitivity that resolved within a week; termed the acute phase. FIG. 2B) During the primed phase (day 7-10) the mice do not display tactile hypersensitivity. The chronic phase can be triggered by intraplantar injection of PGE2 (100 ng, Day 10) which induces prolonged tactile hypersensitivity. It should be noted that the mice that did not undergo paw incision do not develop prolonged allodynia in response to PGE2. (*** $P<0.001$).

FIG. 3A), primed (Day 9; FIG. 3B) and chronic (Day 14; FIG. 3C) phases. Incision increased the expression of ASCT2 and GLS1 relative to the control group only during the primed phase (Day 9; FIG. 3E), but not during the acute (Day 1; FIG. 3D) or chronic (Day 14; FIG. 3F) phases. Unpaired t-test revealed a significant (*$P<0.05$,  $P<0.01$, * $P<0.001$) difference between the control and the incision groups.

FIG. 4D). A single IT administration of teRNA alleviated tactile hypersensitivity in the incision group for at least 7 days. While the control group or the teRNAmm groups did not display any change in their tactile thresholds. Two-way repeated-measure ANOVA revealed a main effect for time ($P<0.001$) and group ($P<0.001$) interaction. Bonferroni post-hoc analysis revealed a significant (## #$P<0.001$) difference between the Incision=>teRNAmm and the control groups (6 mice/group). Bonferroni post-hoc analysis also revealed a significant ( $P<0.01$, * $P<0.001$) difference between the Incision=>teRNAmm and Incision=>teRNA groups (6 mice/group).

DETAILED DESCRIPTION OF THE INVENTION

I. Definitions

Figure 1:
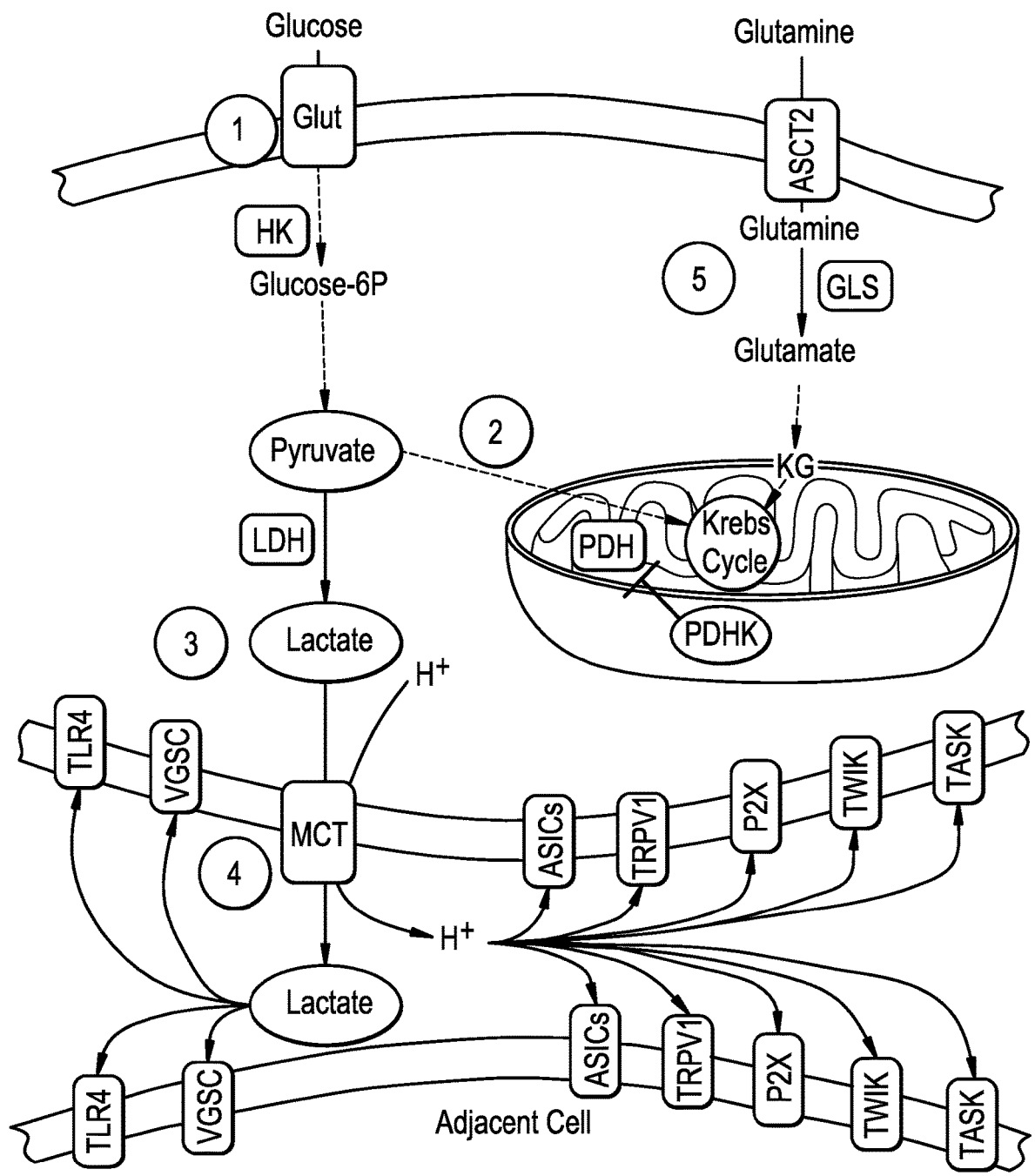
FIG. 1 provides a schematic of some cellular metabolic pathways.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Metabolism is a key biochemical process, inextricably linked to every aspect of cellular function [1]. In recent years, the recognized roles of metabolism have expanded to include regulation of signal transduction pathways and modification of the epigenetic landscape [2,3]. Since metabolic pathways are self-sustaining, altered metabolic states have been shown to maintain aberrant signal transduction and gene expression, which can lead to the development of a variety of neoplastic [4], cardiovascular [5], and neurodegenerative [6] diseases.

As well, metabolism has been found to play a role in chronic pain states, where crucial evidence comes from individuals afflicted with inborn errors of metabolism. Some of these individuals suffer from a variety of chronic pain conditions, such as migraines, visceral, muscle, chest and neuropathic pain [7,8]. Of note, transcriptomic and proteomic studies consistently demonstrate that metabolic genes of sensory neurons are highly altered in preclinical models of chronic pain [9-12].

Cellular metabolism includes (i) the biosynthetic pathway, responsible for the production of complex molecules that constitute a living cell, and (ii) the bioenergetic pathway, linked to energy production [58]. Metabolism associated with energy production is a highly dynamic process where most cells possess the ability to switch energy sources based on their bioenergetic needs. This is especially relevant to neurons which can undergo periods of elevated energy demand following action potentials. Depending on the type of neuron, a single action potential is estimated to consume 107 to 109 ATP molecules [59]. To meet the bioenergetic needs of the cell, neurons are proficient in fully oxidizing glucose and generating over 30 molecules of ATP, most of which are derived from the Krebs cycle in the mitochondria. However, disruption of mitochondrial oxidation results in reliance on glycolysis as an alternative, which is a far less efficient means for generating cellular energy. This is known as aerobic glycolysis or the Warburg effect [60].

Interestingly, Warburg observed that the rate of glycolysis in cancer cells was abnormally high and only a small proportion of the resulting pyruvate was catabolized via mitochondrial oxidative phosphorylation [60]. Pyruvate that is not oxidized in the mitochondria can get converted to lactate by the enzyme lactate dehydrogenase (LDH). This reaction regenerates the cofactor nicotinamide adenine dinucleotide (NAD) in the cytosol which is critical for sustaining glycolysis. Finally, lactate and protons are extruded to the extracellular space via monocarboxylate transporter (MCT), which can lead to the activation of a variety of ion channels and receptors that are expressed in different combinations on sensory neurons. Crucially, these targets are known to sensitize primary afferents (sensory neurons in the peripheral nervous system) and may thus account for conditions of chronic pain [58, 74-76].

Understanding that there may be a link between certain types of metabolism (e.g. aerobic glycolysis) in neurons associated with cancer and chronic pain, the present inventor undertook research into metabolism-associated mechanisms of primary afferent sensitization. The results of this research, some of which is discussed herein, forms the basis of the present invention, namely methods for treating pain by altering neuronal metabolic pathways.

Before discussing the details of the research and the invention, it will be helpful to briefly review relevant metabolic pathways, shown in FIG. 1. These pathways include the following.

(1) Glycolysis is the metabolic process whereby glucose is imported into the cell by the transporter (Glut) and converted to glucose-6-phosphate (glucose-6p) by hexokinase 1 (HK), which in turn generates 2 pyruvate, 2 NADH (NAD$^+$+H) and 2 ATP molecules.

(2) Some of the pyruvate is imported into the mitochondria and converted to acetyl-CoA by pyruvate dehydrogenase (PDH). Acetyl-CoA enters the Krebs cycle where further oxidation can generate around 30 ATP molecules. The rate of PDH enzymatic reaction is attenuated via phosphorylation of PDH by pyruvate dehydrogenase kinase (PDHK).

(3) Pyruvate that is not oxidized is converted to lactate by lactate dehydrogenase (LDH), regenerating NAD (4) Lactate and a proton can be transported to the extracellular space via monocarboxylate transporter (MCT), leading to the activation of a variety of ion channels and receptors that are expressed in different combinations on sensory neurons. Crucially, these targets can sensitize primary afferents via predominantly autocrine and perhaps paracrine signaling.

(5) As an alternative to glycolysis, glutamine is imported into cells through ASCT2 (SLC1A5) and then converted to glutamate by glutaminase (GLS). Glutamate is then transported into the mitochondria where glutamate dehydrogenase converts it to alpha-ketoglutarate (KG) which enters the Krebs cycle to generate around 22 ATP molecules. Disruption of mitochondrial pyruvate oxidation can result in reliance on the oxidation of other substrates such as glutamine. The increase in glutamine oxidation (glutaminolysis) can compensate for the disruption of pyruvate oxidation by maintaining energetics and anaplerosis. Anaplerotic pathways restore homeostasis by replenishing the metabolites lost due to reduced mitochondrial pyruvate oxidation [1].

It should thus be apparent that excess glycolytic flux and reduced mitochondrial pyruvate oxidation in a neuron can lead to overproduction of lactate and protons, which as mentioned above, may lead to sensitization of sensory neurons, such as primary afferents. Sensory neurons express distinct combinations of several types of proton-gated channels which include transient receptor potential vanilloid receptor-1 (TRPV1) [61,77], acid-sensing ion channels (ASICs) [62,63], certain two-pore domain potassium channels (TWIK and TASK) [64] and purinergic P2X receptors [65]. Moreover, lactate enhances the ASIC response to protons [66] and potentiates the electrophysiological properties of voltage-gated sodium channels (VGSCs) [67]. Lactate is also known to potentiate toll-like receptor (TLR) signaling [68].

As summarized above and discussed in detail below, the present invention has identified means for avoiding glycolysis-associated neuronal sensitization. These means are based on increasing the amount of glutamine metabolized in neurons. Indeed, by delving into the nuances of metabolic pathways, the inventor of the present invention has found that by stimulating the metabolic pathway that uses glutamine to produce ATP, and thus minimizing the amount of glycolysis that occurs in the cell, less lactate and protons are produced. As a result, the neurons in which glutamine metabolism has increased exhibit less sensitization of primary afferents, with a related reduction in pain experienced by the subject receiving such treatment.

In particular, the present invention is directed to methods for alleviating pain in a subject generally based on increasing cellular levels of the neutral amino acid transporter ASCT2. This protein, also known as SLC1A5, is a neutral amino acid transporter belonging to the SLC1 family that localizes to the plasma membrane of certain cells, including neurons. ASCT2 preferentially transports glutamine, where glutamine is exchanged, in a Na dependent manner, with other neutral amino acids such as serine, asparagine or threonine [69].

The gene encoding human ASCT2 is located at 19q13.3 and it contains eight exons. Three transcripts for the human gene are reported in the NCBI and Ensemble databases, due to differential translation start sites. The first variant is NM_005628 which represents the longest transcript, comprising 2882 nucleotides and eight exons, which encodes a protein of 541 amino acids. The second variant is NM_001145144 (ENST00000412532.6) which comprises 1750 nucleotides and differs in the 5' UTR from the variant NM_005628. In NM_001145144, the translation start site is downstream of the third exon, generating a shorter protein of 313 aa. The third variant is NM_001145145 (ENST00000434726.6), which comprises 1872 nucleotides and lacks the first exon. It has a different translation start site at 5' of the gene and it encodes a peptide of 339 amino acids [69].

To date, the ASCT2 gene has been found in 56 different organisms and it is present in virtually all vertebrates. The rat, mouse and rabbit orthologous of the human gene have sequence identities of 79, 82, and 85%, respectively. The encoded protein is localized at the plasma membrane of cells and broadly expressed in lung, skeletal muscle, large intestine, kidney, testis, T-cells, brain, and adipose tissue [71,72]. ASCT2 expression increases dramatically in cancers such as colorectal, prostate, hepatic, lung, breast, cervical, ovarian, renal, and brain cancers [70].

Increasing ASCT2 mRNA Translation

The invention is generally directed to methods of alleviating or prophylactically blocking pain in a subject in need thereof, comprising increasing the amount of the ASCT2 mRNA translation in cells of the subject.

Figure 4:
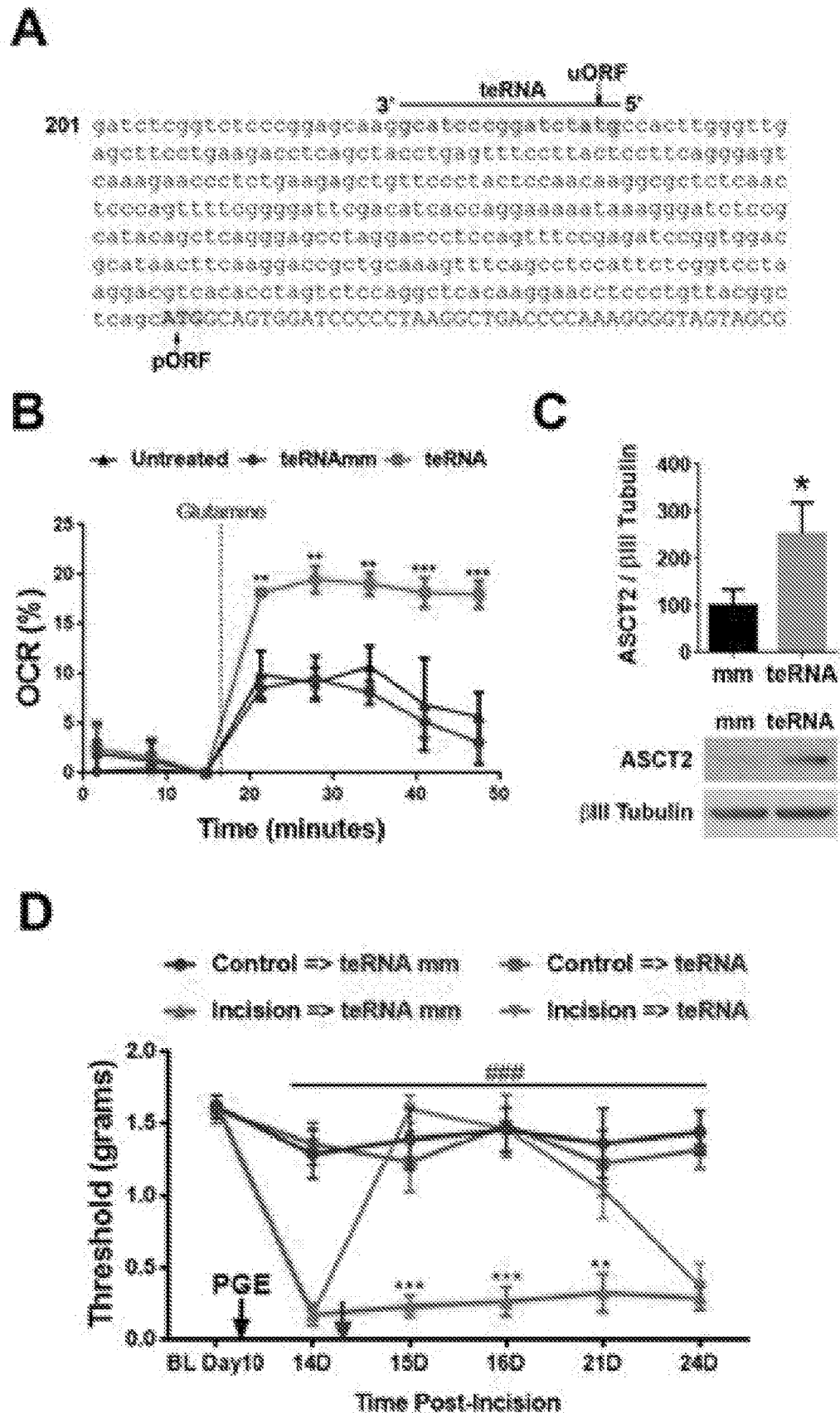
FIG. 4 provides the sequence of the 5' UTR region of the mouse ASCT2 mRNA transcript (FIG. 4A; SEQ ID NO:47) with indications of the primary open reading frame (PORF) and the upstream ORF (uORF) which was targeted using anti-sense oligonucleotide (teRNA). Treatment of DRG cultures with teRNA caused around 20% increase in oxygen consumption rate (OCR) which was sustained for at least 30 mins in response to glutamine addition (FIG. 4B). In contrast, the mismatch teRNA (teRNAmm) or untreated cells display a 10% increase in OCR which diminishes within 30 mins. Two-way repeated-measure ANOVA revealed a main effect for time ($P<0.001$) and group ($P<0.001$) interaction. Bonferroni post-hoc analysis revealed a significant ( $P<0.01$, * $P<0.001$) difference between the teRNA and the other groups. Intrathecal (IT) administration of teRNA causes a robust increase in ASCT2 protein in L4-6 DRGs dissected 24 hrs post injection (FIG. 4C). The control group was treated with mismatch teRNA (mm). Unpaired t-test revealed a significant (*$P<0.01$) difference between the two groups. Mice received IT teRNA or teRNAmm 14 days post plantar incision (4 days post PGE2.

Translation of mRNA in eukaryotic cells is often initiated via a cap-dependent process [14-16,33-37]. The preinitiation complex binds at the 5' cap of an mRNA and scans the 5' untranslated region (UTR) for the presence of an AUG start codon [38-40] (FIG. 4A). Many factors in 5' UTRs can regulate translation [41-44]. The efficiency of the primary open reading frame (pORF) translation can be regulated by the upstream open reading frame (uORF) (FIG. 4A). In some cases, the translation of uORF inhibits translation from the pORF, likely by reducing its accessibility to the preinitiation complex [46,47]. Oligonucleotides that interfere with the uORF translation have been shown to increase translation of the pORF [48,49].

As discussed in detail in the Examples, the present inventor found that oligonucleotides that target and bind the ASCT2 uORF increase the amount of ASCT2 protein in a nerve cell. Further, administration of these oligonucleotides, termed teRNAs (translation enhancing RNAs) herein, can be used to both treat and prevent pain in subjects.

teRNA utilize RNA molecules having a sequence complementary to at least a portion of the target uORF and may contain 2'-O-methyl modifications, which enhances the binding affinity (increases melting temperature, Tm) of the teRNA to the target sequence and decreases their susceptibility to nucleases. A reported below in the Examples, teRNA targeting the ASCT2 gene uORF caused a significant increase the oxygen consumption rate (OCR) in mitochondria in response to glutamine. Glutamine-mediated increase in OCR following teRNA treatment demonstrates increase mitochondrial glutamine oxidation. Moreover, it was determined that IT administration of teRNA caused a significant increase in the expression of ASCT2 in the lumbar 4-6 dorsal root ganglia which innervate the hindpaw. Crucially, IT administration of teRNA alleviated chronic postoperative pain for a week. teRNA thus provides a non-addictive therapeutic approach that is highly target-specific due to the intrinsic property of oligonucleotide base pairing [50-52] and amenable to infrequent dosing due to its extended effect.

Based on these results, and in a first embodiment, the present invention is directed to methods of alleviating pain in a subject, comprising administering a therapeutically effective amount of ASCT2-targeted teRNA to a subject in need thereof. In preferred aspects of this embodiment, the subject is experiencing pain at the time the ASCT2-targeted teRNA is administered. Thus, the administering is a treatment for pain in the subject.

In a second embodiment, the invention is directed to methods of prophylactically blocking pain in a subject, comprising administering a therapeutically effective amount of ASCT2-targeted teRNA to a subject in need thereof. In preferred aspects of this embodiment, the subject is not experiencing pain at the time the ASCT2-targeted teRNA is administered. Thus, the administering is a prophylaxis before pain develops in the subject.

The ASCT2-targeted teRNAs of the invention may be any RNA molecule that binds with specificity and interferes with the regulatory function of ASCT2 mRNA uORF. Such RNA molecules will range in size from about 10 to 40 nucleotides in length.

Suitable ASCT2-targeted teRNAs for use in the treatment and/or prophylaxis of pain in mice include, but are not limited to, the teRNAs provided in Table 1.

TABLE 1

| teRNA Sequences Targeting Mouse ASCT2 | SEQ ID NO: |
|---|---|
| 5'-CAUAGAUCCGGGAUGCCUUG-3' | 1 |
| 5'-CAUAGAUCCGGGAUGCCU-3' | 2 |
| 5'-CAUAGAUCCGGGAUGC-3' | 3 |

Suitable ASCT2-targeted teRNAs for use in the treatment and/or prophylaxis of pain in humans include, but are not limited to, the teRNAs provided in Tables 2-4. As indicated above, there are three ASCT2 variants expressed in human cells. Therefore, the teRNAs used in the therapeutic approaches of the invention will differ depending on the ASCT2 variant being targeted.

TABLE 2

| teRNA Sequences Targeting Human ASCT2 Variant ENST00000594991.5 | SEQ ID NO: |
|---|---|
| 5'-CAUGCCUCAGCCCGGCAGGG-3' | 4 |
| 5'-CAUGCCUCAGCCCGGCAG-3' | 5 |
| 5'-CAUGCCUCAGCCCGGC-3' | 6 |
| 5'-CAUUGUCUGAGAGGCUGGGU-3' | 7 |
| 5'-CAUUGUCUGAGAGGCUGG-3' | 8 |
| 5'-CAUUGUCUGAGAGGCU-3' | 9 |
| 5'-CAUUGUGGGUUCGGGGUGAG-3' | 10 |
| 5'-CAUUGUGGGUUCGGGGUG-3' | 11 |
| 5'-CAUUGUGGGUUCGGGG-3' | 12 |

TABLE 2-continued

| teRNA Sequences Targeting Human ASCT2 Variant ENST00000594991.5 | SEQ ID NO: |
|---|---|
| 5'-CAUGCAGCAAACUUAAUACC-3' | 13 |
| 5'-CAUGCAGCAAACUUAAUA-3' | 14 |
| 5'-CAUGCAGCAAACUUAA-3' | 15 |

TABLE 3

| teRNA Sequences Targeting Human ASCT2 Variant ENST00000434726.6 | SEQ ID NO: |
|---|---|
| 5'-CAUUGUCUGAGAGGCUGGGU-3' | 16 |
| 5'-CAUUGUCUGAGAGGCUGG-3' | 17 |
| 5'-CAUUGUCUGAGAGGCU-3' | 18 |
| 5'-CAUGCCUCAGCCCGGCAGGG-3' | 19 |
| 5'-CAUGCCUCAGCCCGGCAG-3' | 20 |
| 5'-CAUGCCUCAGCCCGGC-3' | 21 |
| 5'-CAUUGUGGGUUCGGGGUGAG-3' | 22 |
| 5'-CAUUGUGGGUUCGGGGUG-3' | 23 |
| 5'-CAUUGUGGGUUCGGGG-3' | 24 |

TABLE 4

| teRNA Sequences Targeting Human ASCT2 Variant ENST00000412532.6 | SEQ ID NO: |
|---|---|
| 5'-CAUGGAGAAACCCCAUCUCU-3' | 25 |
| 5'-CAUGGAGAAACCCCAUCU-3' | 26 |
| 5'-CAUGGAGAAACCCCAU-3' | 27 |
| 5'-CAUUUGUGUUUUGAAAAGAU-3' | 28 |
| 5'-CAUUUGUGUUUUGAAAAG-3' | 29 |
| 5'-CAUUUGUGUUUUGAAA-3' | 30 |
| 5'-CAUGGCAGGGCUCUGGGUAC-3' | 31 |
| 5'-CAUGGCAGGGCUCUGGGU-3' | 32 |
| 5'-CAUGGCAGGGCUCUGG-3' | 33 |
| 5'-CAUAGACUGUAGCAAGGAGA-3' | 34 |
| 5'-CAUAGACUGUAGCAAGGA-3' | 35 |
| 5'-CAUAGACUGUAGCAAG-3' | 36 |
| 5'-CAUAAUCUACUGUGGCUAGA-3' | 37 |
| 5'-CAUAAUCUACUGUGGCUA-3' | 38 |
| 5'-CAUAAUCUACUGUGGC-3' | 39 |
| 5'-CAUUCAAAGAAGAGCCAUAA-3' | 40 |
| 5'-CAUUCAAAGAAGAGCCAU-3' | 41 |
| 5'-CAUUCAAAGAAGAGCC-3' | 42 |
| 5'-CAUCUGAGCUGAGACCUGGA-3' | 43 |

TABLE 4-continued

| teRNA Sequences Targeting Human ASCT2 Variant ENST00000412532.6 | SEQ ID NO: |
|---|---|
| 5'-CAUCUGAGCUGAGACCUG-3' | 44 |
| 5'-CAUCUGAGCUGAGACC-3' | 45 |

Suitable ASCT2-targeted teRNAs for use in the methods of the invention also include sequence variants of the teRNAs set forth in SEQ ID NOs:4-45 having at least 60, 65, 70, 75, 80, 85, 86, 87, 88, 89, 90, 91, 92, 93, 94, 95, 96, 97, 98 or 99% sequence identity over their entire length to a teRNA set forth in one of SEQ ID NOs:4-45 and having the same activity as the teRNA upon which they are based. Alternatively, the sequence variants of the teRNAs set forth in SEQ ID NOs:4-45 having at least 1, 2, 3, 4, 5, 6, 7, 8, 9, 10, 11, 12, 13, 14, 15, 16, 17, 18, 19 or 20 amino acid changes in comparison to a teRNA set forth in one of SEQ ID NOs:4-45 and having the same activity as the teRNA upon which they are based. Each amino acid change may independently be an insertion, deletion or substitution. Each substitution may be a conservative or non-conservative substitution. In some aspects, each amino acid change is a substitution.

The teRNAs may contain one or more of the following chemical modifications or nucleotide analogs: phosphodiester backbone; phosphorothioate backbone; 2-aminopurine; 2,6-diaminopurine; 5-bromo-deoxyuridine; deoxyuridine; inverted dideoxy-T incorporated at the 3'- and/or 5'-end; 5-methyl deoxycytidine; deoxyInosine; super T (5-hydroxybutynl-2'-deoxyuridine); super G (8-aza-7-deazaguanosine); locked nucleic acids; 5-nitroindole; 2'-O-methyl RNA; hydroxymethyl dC; iso-dC; iso-dG; fluoro C, U, A or G; one or more 2'-O-methoxy-ethyl bases. Alternatively, or in addition, the teRNAs may be conjugated with N-acetylgalactosamine (GalNAc) or combined with nanoparticles, such as lipids or polymers, to allow for systemic delivery of the teRNAs to the subject. Alternatively, or in addition, two or more teRNAs may be linked, such as through a short (less than 10 nucleic acids) flexible linker.

Each of the methods of the invention can be practiced in conjunction with administration of a therapeutically effective agent to the subject. As used herein, a "therapeutically effective agent" is an agent that counteracts the metabolic changes in a sensory neuron. An example of a therapeutically effective agent is dichloroacetate (DCA) which has been demonstrated to enhance pyruvate oxidation and alleviate chemotherapy-induced neuropathic pain. Another example is oxamate, which has been shown to prevent the release of metabolites that cause pain [53,54]. 2-Deoxy-d-glucose (2DG) which inhibits glycolytic flux can also be used in conjunction with teRNA [53,54].

Thus, the invention includes methods of alleviating or prophylactically blocking pain in a subject, comprising administering (i) a therapeutically effective amount of ASCT2-targeted teRNA and (ii) one or more of DCA, oxamate and 2DG to a subject in need thereof. In certain aspects, the combination of teRNA with one or more of DCA, oxamate and 2DG is a synergistic combination that is sufficient to alleviate or block a variety of chronic pain states. The ASCT2-targeted teRNA and the one or more of DCA, oxamate and 2DG may be administered to the subject sequentially or concurrently, and in any order.

Increasing ASCT2 Activity

In a third embodiment, the invention is directed to a method of alleviating pain in a subject, comprising increasing the activity of ASCT2 in cells of a subject in need thereof.

In a related embodiment, the invention is directed to methods of prophylactically blocking pain in a subject, comprising increasing the activity of ASCT2 in cells of a subject in need thereof. In preferred aspects of this embodiment, the subject is not experiencing pain at the time the ASCT2-targeted teRNA is administered. Thus, the administering is a prophylaxis before pain develops in the subject.

In non-limiting examples of the manner in which ASCT2 activity might be increased, reference can be made to increasing the stability of ASCT2 in cells of the subject, increasing the trafficking of ASCT2 in cells of the subject, and increasing the transport activity of ASCT2 in cells of the subject.

Increasing ASCT2 Gene Transcription

In a fourth embodiment, the invention is directed to a method of alleviating pain in a subject, comprising increasing the amount of the ASCT2 gene transcription in cells of a subject in need thereof.

In a related embodiment, the invention is directed to methods of prophylactically blocking pain in a subject, comprising increasing the amount of the ASCT2 gene transcription in cells of a subject in need thereof. In preferred aspects of this embodiment, the subject is not experiencing pain at the time the ASCT2-targeted teRNA is administered. Thus, the administering is a prophylaxis before pain develops in the subject.

In each of the embodiments and aspects of the invention, the subject may be one who is experiencing pain, or one in which pain is expected to be experienced in the near future (i.e. within 1, 2, 3, 4, 5, 6, 7, 8, 9, or 10 days, for example), such as a subject that will undergo a surgical procedure or medical treatment that is expected to cause pain. The pain may be acute pain or chronic pain, of any duration or intensity. The pain may be, but is not limited to, one or more of the following types of pain and/or pain associated with one or more of the following conditions or diseases: cancer pain, CIPN, AIDS-related pain, ankylosing spondylitis, arachnoiditis, arthritis, arthrofibrosis, ataxic cerebral palsy, autoimmune atrophic gastritis, autoimmune diseases, avascular necrosis, back pain, breakthrough pain, burning mouth syndrome, bursitis, CARDASIL syndrome, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pancreatitis, coccyx, collapsed lung (pneumothorax), complex regional pain syndrome, corneal neuropathic pain, Crohn's disease, degenerative disc disease, Dercum's disease, dermatomyositis, diabetic peripheral neuropathy, dystonia, Rhlers-Danlos syndrome, endometriosis, eosinophilia-myalgia syndrome, erythromelalgia, failed back surgery syndrome, fibromyalgia, gout, headaches, herniated disc, hydrocephalus, intercostal neuraligia, interstitial cystitis, irritable bowel syndrome, juvenile dermatositis, loin pain-haematuria syndrome, lupus, lyme disease, medullary sponge kidney, meralgia paresthetica, mesothelioma, migraine, mitochondrial disorders, multiple sclerosis, musculoskeletal pain, myofascial pain, myositis, neuropathic pain, occipital neuralgia, osteoarthritis, Paget's disease, parsonage turner syndrome, pelvic pain, peripheral neuropathy, phantom limb pain, pinched nerve, polycystic kidney disease, polymyalgia rhuematica, polymyositis, porphyria, post-herniorraphy pain syndrome, post-mastectomy pain syndrome, post-stroke pain, post-thorocotomy pain syndrome, post-herpetic neuralgia (shingles), post-polio syndrome, primary lateral sclerosis, psoriatic arthritis, pudendal neuralgia, radiculopathy, Raynaud's disease, rheumatoid arthritis, sacroiliac joint dysfunction, sarcoidosis, Scheuemann's kyphosis disease, sciatica, scoliosis, sickle cell, Sjogren's syndrome, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, temporomandibular joint disorder, transverse myelitis, trigeminal neuralgia, ulcerative colitis, vascular pain, vulvodynia and whiplash.

Upon administering the therapeutically effective agents of the invention to a subject experiencing pain, the pain in the subject may be alleviated by at least 5, 10, 15, 20, 25, 30, 35, 40, 45, 50, 55, 60, 65, 70, 75, 80, 85, 90, 95 or 100%, versus a subject experiencing the same pain but not receiving the therapeutically effective agents of the invention. Similarly, upon administering the therapeutically effective agents of the invention to a subject expecting to experience pain, the pain in the subject may be prophylactically blocked by at least 5, 10, 15, 20, 25, 30, 35, 40, 45, 50, 55, 60, 65, 70, 75, 80, 85, 90, 95 or 100%, versus a subject not receiving the therapeutically effective agents of the invention.

The amount of the therapeutically effective agent administered to a subject may vary depending on the identity of the agent, and whether the subject is experiencing pain or expecting to experience pain. The amount of the therapeutically effective agent may also vary depending on the cause of the pain, the location of the pain within the subject, the intensity of the pain, and the length of time the subject has experienced the pain.

When the therapeutically effective agent is ASCT2-targeted teRNA, the therapeutically effective amount of the teRNA will range from about 1 μg to about 1 mg when administered intrathecally, e.g. administered directly to the trigeminal and/or sensory ganglia. However, higher doses may be required when administered via other routes. The therapeutically effective dose will generally range from about 1 μg to about 10 mg of ASCT2-targeted teRNA.

The therapeutically effective agents of the invention may be formulated as pharmaceutical compositions comprising the therapeutically effective agent and one or more carriers, diluents and excipients.

The therapeutically effective agents and pharmaceutical compositions of the invention may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In preferred aspects of the invention, the therapeutically effective agents and pharmaceutical compositions are administered to a subject by direct administration to the trigeminal and/or dorsal root ganglia. This preferred route of administration is based on confirmed efficacy of teRNA in alleviating and/or preventing the development of diverse chronic pain states in preclinical models.

Administration frequencies for the therapeutically effective agents and pharmaceutical compositions of the present invention include 4, 3, 2 or once daily, every other day, every third day, every fourth day, every fifth day, every sixth day, once weekly, every eight days, every nine days, every ten days, bi-weekly, monthly and bi-monthly. The duration of time over which the therapeutically effective agents are administered to a subject will be based on the type of pain being treated and will be best determined by the attending physician. However, continuation of pain treatment is contemplated to last for a number of days, weeks, months or years. Indeed, in some instances, treatment may continue for the entire life of the subject.

Depending on the means of administration, the agents and compositions may be administered all at once, such as with an oral formulation in a capsule or liquid, or slowly over a period of time, such as with an intramuscular or intravenous administration.

In each of the embodiments and aspects of the invention, the subject is a human, a non-human primate, bird, horse, cow, goat, sheep, a companion animal, such as a dog, cat or rodent, or other mammal.

III. Examples

A series of experiments were conducted in mice to determine whether changes in metabolic genes known to regulate pyruvate and glutamine oxidation could be detected when the mouse was experiencing one or more types of pain.

Hyperalgesic Priming Model

Figure 2:
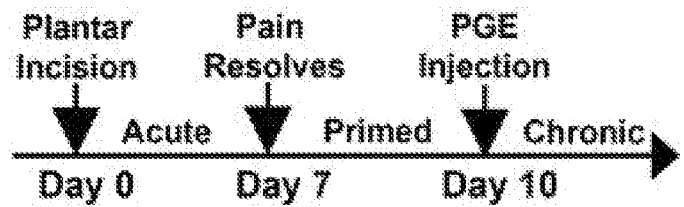
FIG. 2 provides a hyperalgesic priming model using plantar incision as the initial stimulus.
Figure 2:
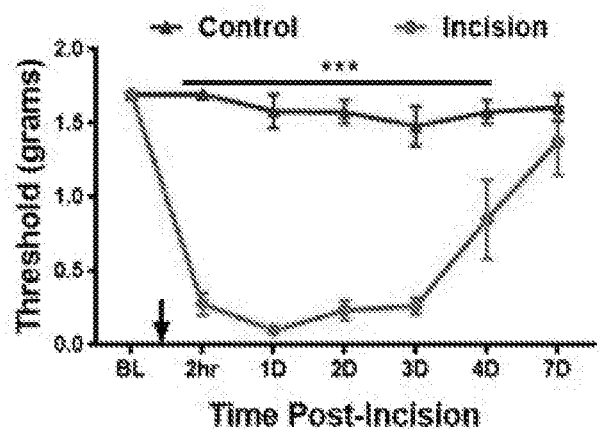
Figure 2:
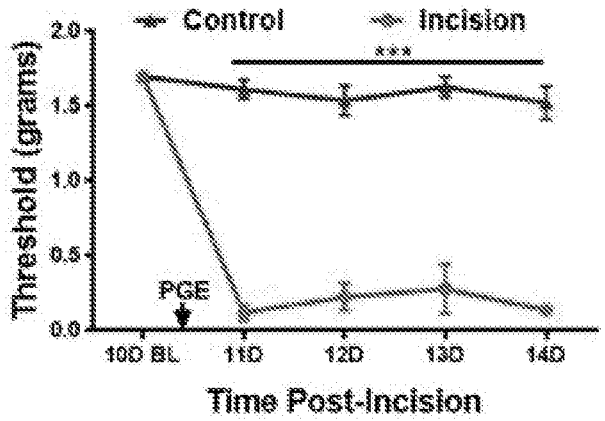

The hyperalgesic priming model was utilized in the experiments because it is well-characterized and used to study the neuroplasticity underlying persistent pain sensitization and the transition of acute pain to chronic pain [13-17]. As shown at the top FIG. 2, the model is comprised of three phases. 1) The acute phase, also called the induction phase, causes transient tactile hypersensitivity in response to various pro-nociceptive compounds and resolves within a week. The hindpaw plantar incision model was used for the acute phase, which comprises incision of the skin, the underlying fascia, and the plantar flexor digitorum brevis muscle as the initial injury [18,19]. This model was selected since it lacks injury to major peripheral nerves and typically resolves within a week. 2) The primed phase follows the acute phase. The animals are not hypersensitive and this phase can last for at least 3 weeks. 3) The chronic phase, also called the maintenance phase, is expressed by plantar injection of prostaglandin E2 or other stimuli and has been demonstrated to last for at least 2 months [13,14, 16,20,21].

Results from experiments during the acute phase demonstrated that pain associated with the incisional injury resolved within a week. In this experiment, mice received plantar incision and their tactile thresholds were determined using von Frey filaments. Mice were placed in small cages with a mesh floor individually. Calibrated monofilaments of differing forces are applied perpendicularly to the hind paw. Withdraws, licking or flinching of the paw in response to the filament is considered a positive response. The results are provided in FIG. 2A where "Threshold (grams)" on the y-axis represents the amount of force required for the mice to withdraw the hindpaw before (baseline, BL) and after the incision. Reduced withdrawal threshold indicates increased pain. Time Post-Incision on the x-axis shows time points that include baseline (BL), two hours post-incision, and 1, 2, 3, 4 and 7 days post-incision.

Results from experiments during the chronic phase demonstrated that pain can be induced via plantar injection of prostaglandin E2 (PGE2; 100 ng, Day 10). In this experiment, the same mice used in the acute phase were allowed to recover and on Day 10 received intraplantar PGE2. The results are provided in FIG. 2B where "Threshold (grams)" on the y-axis represents the amount of force required for the mice to withdraw their hindpaw which is an indication of tactile hypersensitivity and pain. Time Post-Incision on the x-axis shows time points that include baseline measurements before the intraplantar administration of PGE2 (10D BL) and 11, 12, 13 and 14 days post-incision. 1, 2, 3 and 4 days post-PGE2 injection, *** P<0.001. Baseline measurement demonstrated that prior to PGE2 injection the mice did not display tactile hypersensitivity. PGE2 injection caused profound allodynia in mice that had plantar incision. In contrast, mice that did not undergo paw incision did not develop prolonged allodynia in response to PGE2.

Western Blot Analyses of Metabolic Protein Production

Western blot (WB) analyses were performed to examine changes in metabolic genes that are known to regulate pyruvate and glutamine oxidation [22-25]. In these experiments, lumbar 4-6 dorsal root ganglia (L4-6 DRGs) which innervate the hindpaw were dissected on Day 1, 9 and 14 post-plantar incisions (as described above). Protein was extracted from the L4-6 DRGs in lysis buffer (50 mM Tris HCl, 1% Triton X-100, 150 mM NaCl, and 1 mM EDTA at pH 7.4) containing protease and phosphatase inhibitor mixtures with an ultrasonicator on ice, and cleared of cellular debris by centrifugation at 14,000 relative centrifugal force for 15 min at 4° C. Fifteen micrograms of protein per well were loaded and separated by standard 7.5% or 10% SDS-PAGE. Proteins were transferred to Immobilon-P membranes (Millipore Sigma, Cat #IPVH00010) and then blocked with 5% dry milk for 3 h at room temperature. The blots were incubated with primary antibody overnight at 4° C. and detected the following day with donkey anti-rabbit or goat anti-mouse antibody conjugated to horseradish peroxidase (1:10,000, Jackson Immunoresearch, Cat #711-036-152, Cat #115-036-062). Signal was detected by enhanced chemiluminescence on films. For assessment of phospho-proteins, membranes were stripped and reprobed for total-protein of interest for normalization. Densitometric analyses were done using UN-SCAN-IT 7.1 software (Silk Scientific Corp.). Primary antibodies include phospho-PDH Ser300, phospho-PDH Ser2093, PDP1 (1:1000, Millipore Sigma, Cat #ABS192, ABS204, 07-1223), PDH, ASCT2, PDHK1 (1:1000 Cell Signaling Technology, Cat #3205, 5345, 3820) and beta-III-tubulin (1:50,000 Promega, Cat #G7121).

Figure 3:
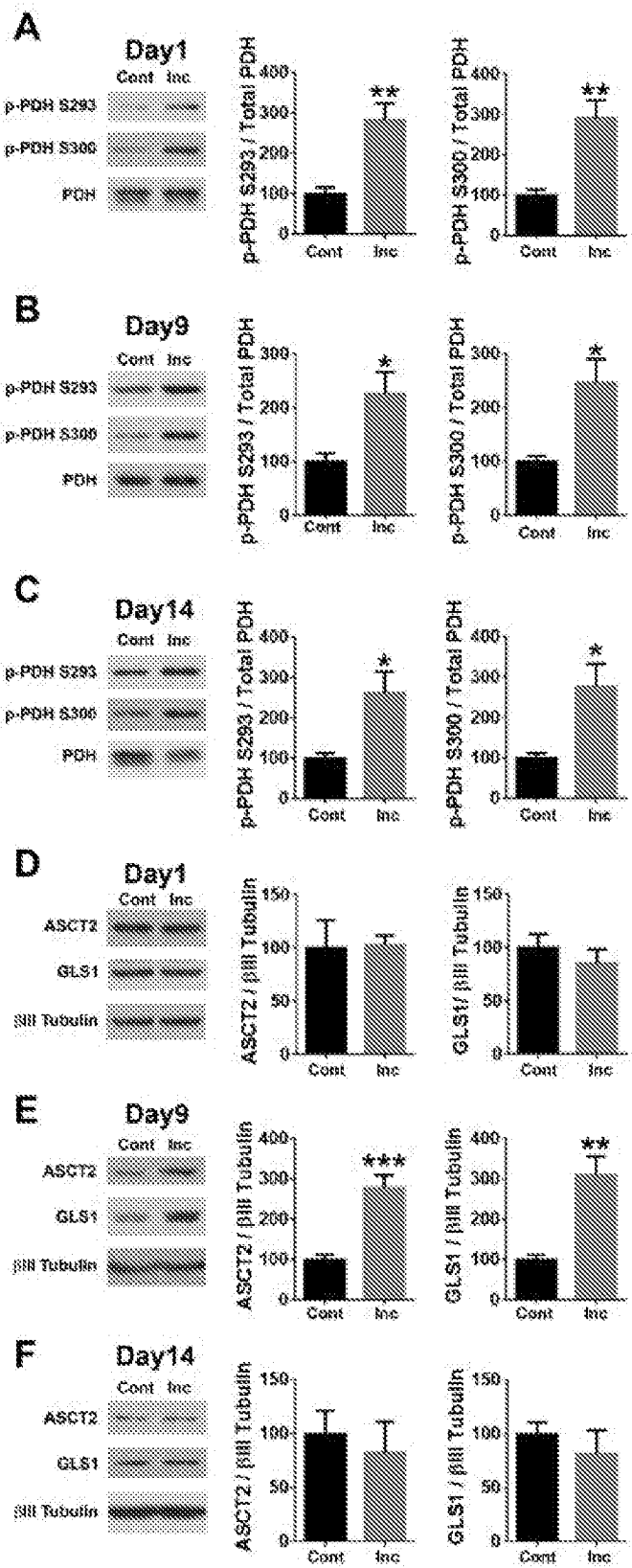
FIG. 3 provides the results of Western blot analysis of the lumbar 4-6 dorsal root ganglia (L4-6 DRGs), demonstrating that following paw incision (Inc) the phosphorylation of pyruvate dehydrogenase (PDH) increases on S293 and S300 relative to control (Cont) during the acute (Day 1.

The results shown in FIG. 3 demonstrate that surgical trauma enhanced the phosphorylation of pyruvate dehydrogenase (PDH) on serine 293 and 300 (FIGS. 3A, 3B & 3C), which is known to limit mitochondrial pyruvate oxidation which leads to the conversion of pyruvate. The extrusion of lactate and protons from sensory neurons leads to their sensitization [22]. However, Western blot analysis also revealed that only during the primed phase (Day 9) L4-6 DRGs show increased expression of the glutamine transporter ASCT2 and the glutamine catabolizing enzyme GLS1 (FIG. 3E). The expression of ASCT2 or GLS1 were not significantly different from the control group post-incision in DRGs dissected on days 1 and 14 (FIGS. 3D & 3F). These data suggested that the anaplerotic reaction of glutamine oxidation compensates for the decline in mitochondrial pyruvate oxidation. The results suggested that augmented expression of ASCT2 can serve as an endogenous anti-nociceptive mechanism which allows for pain to resolve.

Increased Translation of ASCT2

A therapeutic strategy that increases the translation of ASCT2 mRNA might alleviate post-surgical pain by increasing glutamine oxidation with a concomitant decrease in pyruvate oxidation and reduced neuronal sensitization. As discussed above, translation in eukaryotic cells is often initiated via a cap-dependent process [14-16,33-37]. The preinitiation complex binds at the 5' cap of an mRNA and scans the 5' untranslated region (UTR) for the presence of an AUG start codon [38-40]. The efficiency of the primary open reading frame (PORF) translation has been shown to be regulated by the upstream open reading frame (uORF) [45]. The translation of uORFs inhibits translation from the pORF, likely by reducing its accessibility to the preinitiation complex [46,47]. Oligonucleotides that interfere with the uORF have been shown to increase translation of the pORF [48,49]. Hence, a highly innovative RNA-based therapeutic approach was developed, termed teRNA (translation enhancing RNA) herein. teRNA molecules bind to the uORF and thus induce translation of the pORF. The RNA molecules contain 2'-O-methyl modifications which enhances the binding affinity (increases melting temperature, Tm) of the teRNA molecules to a target sequence and decreases their susceptibility to nucleases.

ASCT2 teRNA and mismatch teRNA (teRNAmm) molecules were prepared based on the sequence of the 5' UTR region of the mouse ASCT2 mRNA transcript (FIG. 4A). The teRNA molecule is an anti-sense oligonucleotide that binds to the uORF site and interferes with translation from this site, permitting increased translation of the pORF and increased levels of the ASCT2 protein in cells. The teRNAmm molecule contains several missense mutations that does not bind to the uORF. In particular, the teRNA molecule having the following sequence: 5'-CAUA-GAUCCGGGAUGC-3' (SEQ ID NO:3) and the teRNAmm molecule having the following sequence: 5'-CAUAC-UACGCCGUAGC-3' (SEQ ID NO:46) were prepared.

In this experiment, mice were injected with 1 μg of teRNA or teRNAmm intrathecally (IT). The next day L4-6 DRGs were dissected and acutely dissociated for extracellular flux analysis. One day post teRNA and teRNA mm injection L4-6 DRGs were dissected and proteins were extracted for western blot analysis. In an independent experiment, mice received plantar incision and were allowed to recover. On day 10 baseline measurements were performed, which was followed by intraplantar injection of PGE2. Allodynia testing was preformed form on days 14, 15, 21 and 24. Intrathecal teRNA or teRNAmm (1 μg) were injected on day 14 following the allodynia testing. The results from the experiments are presented in FIGS. 4B-4D.

The results presented in FIG. 4B demonstrate that DRG cultures from mice treated with teRNA caused around 20% increase in oxygen consumption rate (OCR) which was sustained for at least 30 mins in response to glutamine addition. In contrast, DRG culture cells from teRNAmm-treated mice or DRG culture cells from untreated mice displayed a 10% increase in OCR which diminishes within 30 mins. In this experiment, L4-6 DRGs were dissected form naïve, teRNAmm and teRNA treated mice. Lumbar 4-6 DRGs were placed in Hank's Buffered Salt Solution (HBSS, Thermo Fisher, Cat #14170112) on ice. The ganglia were dissociated enzymatically with collagenase A (1 mg/ml, 25 min, Millipore Sigma, Cat #10103578001) and collagenase D (1 mg/ml, Millipore Sigma, Cat #11088858001) with papain (30 U/ml, Millipore Sigma, Cat #10108014001) for 20 min at 37° C. To eliminate debris and large diameter sensory neurons, 70 μm (Thermo Fisher, Cat #087712) cell strainers were used. The dissociated cells were resuspended in DMEM/F12 (Thermo Fisher, Cat #10565042) containing 1× pen-strep (Thermo Fisher, Cat #15070063) and 10% fetal bovine serum (Millipore Sigma, Cat #F2442). The cells were plated in Seahorse XFp Cell Culture Miniplate (Agilent, Cat #103025-100). These cultures were incubated overnight at 37° C. in a humidified 95% air/5% CO2 incubator. The metabolic changes were characterized by analyzing the glycolysis and oxidative phosphorylation rates of sensory neurons using extracellular flux analyzer, Seahorse XFp (Agilent). Dissociated L4-6 primary afferents were incubated in DMEM (Millipore Sigma, Cat #D5030) without glutamine, pyruvate or glucose, Baseline oxygen consumption rate (OCR) measurements were followed by the addition of glutamine (2 mM). The baseline OCR values were subtracted from each of the other values to determine glutamine oxidation-dependent OCR. Two-way repeated-measure ANOVA revealed a main effect for time ($P<0.001$) and group ($P<0.001$) interaction. Bonferroni post-hoc analysis revealed a significant ( $P<0.01$, * $P<0.001$) difference between the teRNA and the other groups.

The results presented in FIG. 4C demonstrate intrathecal (IT) administration of teRNA causes a robust increase in ASCT2 protein in L4-6 DRGs dissected 24 hrs post injection. In this experiment, Western blot analysis was performed on proteins isolated from L4-6 DRGs. The control group was proteins isolated L4-6 DRGs from mice treated with teRNAmm (mm). Unpaired t-test revealed a significant (*$P<0.01$) difference between the two groups.

The results presented in FIG. 4D are from an experiment where mice received IT teRNA or teRNAmm 14 days post plantar incision (4 days post PGE2), following the procedure described above for intraplantar injection of PGE2. A single IT administration of teRNA alleviated tactile hypersensitivity in the incision group for at least 7 days. While the control group or the teRNAmm groups did not display any change in their tactile thresholds. Two-way repeated-measure ANOVA revealed a main effect for time ($P<0.001$) and group ($P<0.001$) interaction. Bonferroni post-hoc analysis revealed a significant (## #$P<0.001$) difference between the Incision=>teRNAmm and the control groups 6 mice/group). Bonferroni post-hoc analysis also revealed a significant ( $P<0.01$, * $P<0.001$) difference between the Incision=>teRNAmm and Incision=>teRNA (6 mice/group). It can be noted teRNA did not affect the tactile thresholds of the control group. teRNA provided a non-addictive therapeutic approach that is highly target-specific due to the intrinsic property of oligonucleotide base pairing [50-52] and amenable to infrequent dosing due to its extended effect.

Treatment of Chemotherapy-Induced Painful Peripheral Neuropathy (CIPN)

Chemotherapy-induced painful peripheral neuropathy (CIPN) affects up to 80% of patients who receive anticancer therapy. This adverse effect can be severe enough for patients to either reduce the dosage of anticancer treatment or stop the treatment altogether. CIPN has been recently demonstrated to be caused by a reduction in pyruvate oxidation which leads to the extrusion of metabolites (lactate and protons) that cause pain by sensitization of peripheral afferents [53,54].

The chemotherapeutic bortezomib upregulates lactate dehydrogenase A (LDHA) and pyruvate dehydrogenase kinase 1 (PDHK1), which enhance the production of lactate and repress pyruvate oxidation, respectively. Treatment of subjects having cancer with bortezomib can lead to bortezomib-induced CIPN. Thus, a mouse model of bortezomib-induced CIPN was used in the following experiment.

teRNA was administered to mice which have developed neuropathic pain due to bortezomib treatment. In this experiment, mice were treated with intraperitoneal 0.2 mg/kg of bortezomib (Millipore Sigma, Cat #5.04314.0001) for 5 consecutive days for a total dose of 1 mg/kg [73]. The vehicle group received intraperitoneal saline for 5 consecutive days. The mice that receive bortezomib develop profound allodynia. The efficacy of teRNA for treating and preventing the development of bortezomib-induced neuropathic pain was explored. The results from the experiments are presented in FIGS. 5A-5C.

Figure 5:
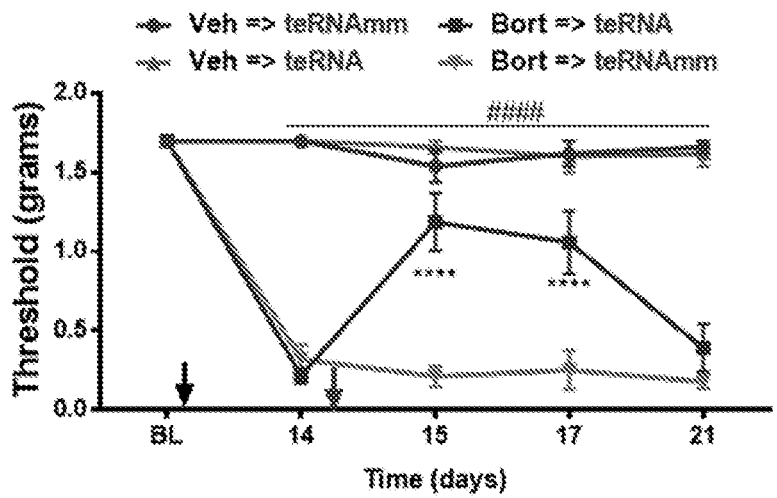
FIG. 5 provides the results of experiments in which mice were treated with the chemotherapeutic, bortezomib. Treatment with bortezomib (bort) from day 0-4 (black arrow) led to the development of severe neuropathic pain. IT treatment with teRNA (blue arrow) on day 14 reversed the bortezomib-induced neuropathic pain (FIG. 5A). The control group (mismatch teRNA, teRNAmm) did not impact the tactile thresholds. IT treatment with teRNA on days 7, 9 and 11 alleviated existing neuropathic pain for at least 21 days post the initiation of bortezomib treatment (FIG. 5B). Co-treatment of mice with teRNA (days 0, 2 and 4) with bortezomib (days 0-4) prevented the development of neuropathic pain (FIG. 5C). Bonferroni post-hoc analysis revealed a significant (####$P<0.0001$) difference between the IP Bort=>IT teRNAmm and the control groups (6 mice/group). Bonferroni post-hoc analysis also revealed a significant (**** $P<0.0001$) difference between the IP Bort=>IT teRNAmm and IP Bort=>IT teRNA groups (6 mice/group).
Figure 5:
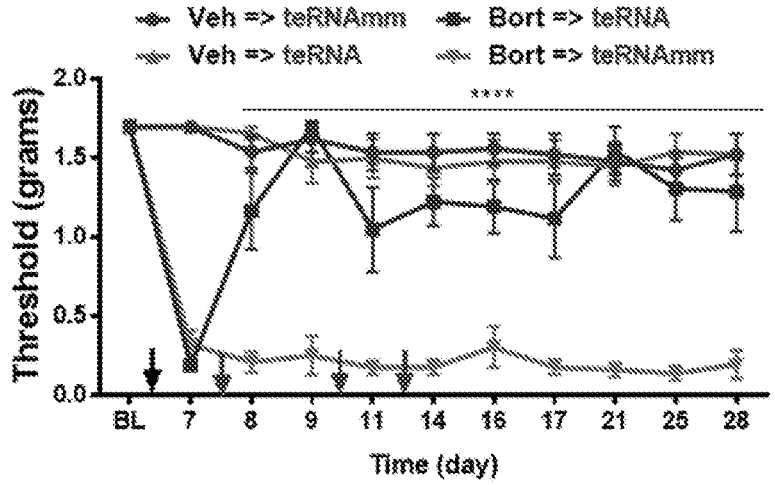
Figure 5:
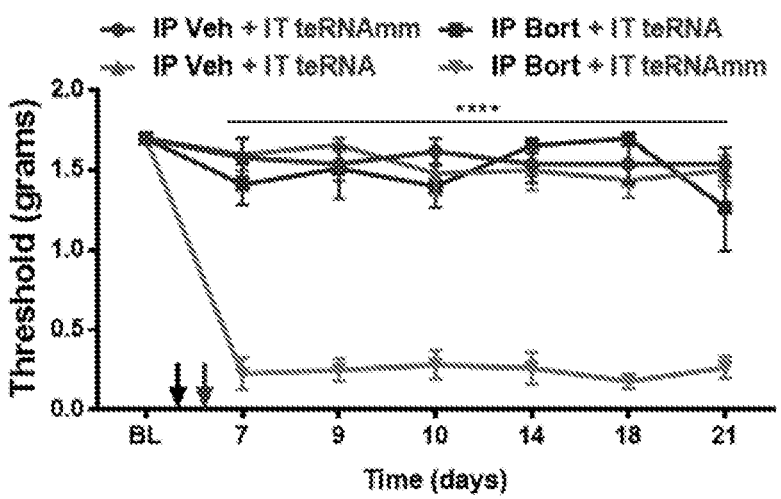

The results presented in FIG. 5A demonstrate that a single IT injection of teRNA (1 µg) alleviated bortezomib-induced neuropathic pain for several days. Treatment with bortezomib (bort) from day 0-4 (black arrow) led to the development of severe neuropathic pain. Baseline thresholds were measured on day 0 and allodynia was tested on days 14, 15, 17 and 21. Intrathecal (IT) treatment with teRNA (blue arrow) on day 14 (following allodynia testing) reversed the bortezomib-induced neuropathic pain (FIG. 5A). The control group (teRNAmm) (1 µg) did not impact the tactile thresholds.

In a second experiment, mice were treated with either saline or bortezomib on days 0-4 (intraperitoneal 0.2 mg/kg of bortezomib for 5 consecutive days for a total dose of 1 mg/kg). On day 7 mice that received bortezomib developed profound neuropathic pain. IT administration of teRNA (1 µg) on days 7, 9 and 11 post-bortezomib treatment led to a prolonged pain relief that lasted at least 2 weeks (FIG. 5B). The control group received IT teRNAmm (1 µg) which did not impact the bortezomib-induced neuropathic pain. These data demonstrate that teRNA can be disease-modifying where repeated treatment can potentially reverse the course of the disease.

To determine if teRNA can prevent the development of chemotherapy-induced neuropathic pain, mice were co-treated with IT teRNA (days 0, 2 and 4) and intraperitoneal (IP) bortezomib (days 0-4) (intraperitoneal 0.2 mg/kg of bortezomib for 5 consecutive days for a total dose of 1 mg/kg). Treatment with teRNA prevented the development of bortezomib-induced neuropathic pain revealing the utility of teRNA for the prevention of chemotherapy-induced neuropathic pain (FIG. 5C). Bonferroni post-hoc analysis revealed a significant (## ##$P<0.0001$) difference between the IP Bort=>IT teRNAmm and the control groups (6 mice/group). Bonferroni post-hoc analysis also revealed a significant (**** $P<0.0001$) difference between the IP Bort=>IT teRNAmm and IP Bort=>IT teRNA groups (6 mice/group).

These results collectively show that teRNA which enhances the translation of ASCT2 is effective for the treatment and prevention of vastly distinct chronic pain conditions.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Lehninger, A. L., Nelson, D. L. & Cox, M. M. Lehninger principles of biochemistry (W.H. Freeman, New York, 2013).
2. Yuan, H. X., Xiong, Y. & Guan, K. L. Nutrient sensing, metabolism, and cell growth control. Mol Cell 49, 379-87 (2013).
3. Tato, I., Bartrons, R., Ventura, F. & Rosa, J. L. Amino acids activate mammalian target of rapamycin complex 2 (mTORC2) via PI3K/Akt signaling. J Biol Chem 286, 6128-42 (2011).
4. Yang, M., Soga, T. & Pollard, P. J. Oncometabolites: linking altered metabolism with cancer. J Clin Invest 123, 3652-8 (2013).
5. Singh, S., Schwarz, K., Horowitz, J. & Frenneaux, M. Cardiac energetic impairment in heart disease and the potential role of metabolic modulators: a review for clinicians. Circ Cardiovasc Genet 7, 720-8 (2014).
6. Cai, H. et al. Metabolic dysfunction in Alzheimer's disease and related neurodegenerative disorders. Curr Alzheimer Res 9, 5-17 (2012).
7. Cohen, B. H. & Gold, D. R. Mitochondrial cytopathy in adults: what we know so far. Cleve Clin J Med 68, 625-6, 629-42 (2001).
8. Saudubray, J. M., Van den Berghe, G. & Walter, J. Inborn metabolic diseases: diagnosis and treatment (Springer, Berlin, 2012).
9. Melemedjian, O. K., Yassine, H. N., Shy, A. & Price, T. J. Proteomic and functional annotation analysis of injured peripheral nerves reveals ApoE as a protein upregulated by injury that is modulated by metformin treatment. Mol Pain 9, 14 (2013).
10. Huang, H. L. et al. Proteomic profiling of neuromas reveals alterations in protein composition and local protein synthesis in hyper-excitable nerves. Mol Pain 4, 33 (2008).
11. Niederberger, E. & Geisslinger, G. Proteomics in neuropathic pain research. Anesthesiology 108, 314-23 (2008).
12. Costigan, M. et al. Replicate high-density rat genome oligonucleotide microarrays reveal hundreds of regulated genes in the dorsal root ganglion after peripheral nerve injury. BMC Neurosci 3, 16 (2002).
13. Ferrari, L. F., Araldi, D. & Levine, J. D. Distinct terminal and cell body mechanisms in the nociceptor mediate hyperalgesic priming. J Neurosci 35, 6107-16 (2015).
14. Melemedjian, O. K. et al. IL-6- and NGF-induced rapid control of protein synthesis and nociceptive plasticity via convergent signaling to the eIF4F complex. J Neurosci 30, 15113-23 (2010).
15. Melemedjian, O. K. & Khoutorsky, A. Translational control of chronic pain. Prog Mol Biol Transl Sci 131, 185-213 (2015).
16. Melemedjian, O. K. et al. Local translation and retrograde axonal transport of CREB regulates IL-6-induced nociceptive plasticity. Mol Pain 10, 45 (2014).
17. Reichling, D. B. & Levine, J. D. Critical role of nociceptor plasticity in chronic pain. Trends Neurosci 32, 611-8 (2009).
18. Brennan, T. J., Vandermeulen, E. P. & Gebhart, G. F. Characterization of a rat model of incisional pain. Pain 64, 493-501 (1996).
19. Brennan, T. J. Postoperative Models of Nociception. ILAR J 40, 129-136 (1999).
20. Ferrari, L. F., Bogen, O., Reichling, D. B. & Levine, J. D. Accounting for the delay in the transition from acute to chronic pain: axonal and nuclear mechanisms. J Neurosci 35, 495-507 (2015).
21. Aley, K. O., Messing, R. O., Mochly-Rosen, D. & Levine, J. D. Chronic hypersensitivity for inflammatory 21. nociceptor sensitization mediated by the epsilon isozyme of protein kinase C. J Neurosci 20, 4680-5 (2000).
22. Yang, C. et al. Analysis of hypoxia-induced metabolic reprogramming. Methods Enzymol 542, 425-55 (2014).
23. Semenza, G. L. Targeting HIF-1 for cancer therapy. Nat Rev Cancer 3, 721-32 (2003).
24. van Geldermalsen, M. et al. ASCT2/SLC1A5 controls glutamine uptake and tumour growth in triple-negative basal-like breast cancer. Oncogene (2015).
25. Weinberg, F. et al. Mitochondrial metabolism and ROS generation are essential for Kras-mediated tumorigenicity. Proc Natl Acad Sci USA 107, 8788-93 (2010).
26. Laboureyras, E., Chateauraynaud, J., Richebe, P. & Simonnet, G. Long-term pain vulnerability after surgery in rats: prevention by nefopam, an analgesic with antihyperalgesic properties. Anesth Analg 109, 623-31 (2009).
27. Sun, E. C., Darnall, B. D., Baker, L. C. & Mackey, S. Incidence of and Risk Factors for Chronic Opioid Use Among Opioid-Naive Patients in the Postoperative Period. JAMA Intern Med 176, 1286-93 (2016).
28. Cicero, T. J., Ellis, M. S., Surratt, H. L. & Kurtz, S. P. The changing face of heroin use in the United States: a retrospective analysis of the past 50 years. JAMA Psychiatry 71, 821-6 (2014).
29. Jones, C. M. Heroin use and heroin use risk behaviors among nonmedical users of prescription opioid pain relievers-United States, 2002-2004 and 2008-2010. Drug Alcohol Depend 132, 95-100 (2013).
30. Lankenau, S. E. et al. Initiation into prescription opioid misuse amongst young injection drug users. Int J Drug Policy 23, 37-44 (2012).
31. Rudd, R. A., Noah Aleshire, Jon E. Zibbell, and R. Matthew Gladden. Increases in Drug and Opioid Overdose Deaths-United States, 2000-2014. Centers for Disease Control and Prevention (2016).
32. Florence, C. S., Zhou, C., Luo, F. & Xu, L. The Economic Burden of Prescription Opioid Overdose, Abuse, and Dependence in the United States, 2013. Med Care 54, 901-6 (2016).
33. Melemedjian, O. K. et al. Targeting adenosine monophosphate-activated protein kinase (AMPK) in preclinical models reveals a potential mechanism for the treatment of neuropathic pain. Mol Pain 7, 70 (2011).
34. Melemedjian, O. K. et al. mTORC1 inhibition induces pain via IRS-1-dependent feedback activation of ERK. Pain 154, 1080-91 (2013).
35. Melemedjian, O. K., Mejia, G. L., Lepow, T. S., Zoph, O. K. & Price, T. J. Bidirectional regulation of P body formation mediated by eIF4F complex formation in sensory neurons. Neurosci Lett 563, 169-74 (2014).
36. Melemedjian, O. K. & Price, T. J. Dendritic spine plasticity as an underlying mechanism of neuropathic pain: commentary on Tan et al. Exp Neurol 233, 740-4 (2012).
37. Melemedjian, O. K. et al. BDNF regulates atypical PKC at spinal synapses to initiate and maintain a centralized chronic pain state. Mol Pain 9, 12 (2013).
38. Sonenberg, N. & Hinnebusch, A. G. Regulation of translation initiation in eukaryotes: mechanisms and biological targets. Cell 136, 731-45 (2009).
39. Kozak, M. Evaluation of the "scanning model" for initiation of protein synthesis in eucaryotes. Cell 22, 7-8 (1980).
40. Kozak, M. Pushing the limits of the scanning mechanism for initiation of translation. Gene 299, 1-34 (2002).
41. Xue, S. & Barna, M. Specialized ribosomes: a new frontier in gene regulation and organismal biology. Nat Rev Mol Cell Biol 13, 355-69 (2012).
42. Pichon, X. et al. RNA binding protein/RNA element interactions and the control of translation. Curr Protein Pept Sci 13, 294-304 (2012).
43. Araujo, P. R. et al. Before It Gets Started: Regulating Translation at the 5' UTR. Comp Funct Genomics 2012, 475731 (2012).
44. Kozak, M. Regulation of translation via mRNA structure in prokaryotes and eukaryotes. Gene 361, 13-37 (2005).
45. Barbosa, C., Peixeiro, I. & Romao, L. Gene expression regulation by upstream open reading frames and human disease. PLOS Genet 9, e1003529 (2013).
46. Lee, S. et al. Global mapping of translation initiation sites in mammalian cells at single-nucleotide resolution. Proc Natl Acad Sci USA 109, E2424-32 (2012).
47. Calvo, S. E., Pagliarini, D. J. & Mootha, V. K. Upstream open reading frames cause widespread reduction of protein expression and are polymorphic among humans. Proc Natl Acad Sci USA 106, 7507-12 (2009).
48. Liang, X.-h. et al. Translation efficiency of mRNAs is increased by antisense oligonucleotides targeting upstream open reading frames. Nature Biotechnology 34, 875 (2016).
49. Liang, X. H., Shen, W. & Crooke, S. T. Specific Increase of Protein Levels by Enhancing Translation Using Antisense Oligonucleotides Targeting Upstream Open Frames. Adv Exp Med Biol 983, 129-146 (2017).
50. Khorkova, O. & Wahlestedt, C. Oligonucleotide therapies for disorders of the nervous system. Nat Biotechnol 35, 249-263 (2017).
51. Burnett, J. C. & Rossi, J. J. RNA-based therapeutics: current progress and future prospects. Chem Biol 19, 60-71 (2012).
52. Zhou, J. & Rossi, J. Aptamers as targeted therapeutics: current potential and challenges. Nat Rev Drug Discov 16, 181-202 (2017).
53. Ludman, T. & Melemedjian, O. K. Bortezomib and metformin opposingly regulate the expression of hypoxia-inducible factor alpha and the consequent development of chemotherapy-induced painful peripheral neuropathy. Mol Pain 15, 1744806919850043 (2019).
54. Ludman, T. & Melemedjian, O. K. Bortezomib-induced aerobic glycolysis contributes to chemotherapy-induced painful peripheral neuropathy. Mol Pain 15, 1744806919837429 (2019)
55. Bennett, G. J., T. Doyle and D. Salvemini (2014). "Mitotoxicity in distal symmetrical sensory peripheral neuropathies." Nat Rev Neurol 10(6): 326-336.
56. Sisignano, M., R. Baron, K. Scholich and G. Geisslinger (2014). "Mechanism-based treatment for chemotherapy-induced peripheral neuropathic pain." Nat Rev Neurol 10(12): 694-707.
57. Boyette-Davis, J. A., E. T. Walters and P. M. Dougherty (2015). "Mechanisms involved in the development of chemotherapy-induced neuropathy." Pain Manag 5(4): 285-296.
58. Lehninger, A. L., D. L. Nelson and M. M. Cox (2013). Lehninger principles of biochemistry. New York, W.H. Freeman.
59. Lewis, J. E., K. M. Gilmour, M. J. Moorhead, S. F. Perry and M. R. Markham (2014). "Action potential energetics at the organismal level reveal a trade-off in efficiency at high firing rates." J Neurosci 34(1): 197-201.
60. Warburg, O. (1925). "The Metabolism of Carcinoma Cells." The Journal of Cancer Research 9(1): 148-163.

61. Caterina, M. J., M. A. Schumacher, M. Tominaga, T. A. Rosen, J. D. Levine and D. Julius (1997). "The capsaicin receptor: a heat-activated ion channel in the pain pathway." Nature 389(6653): 816-824.
62. Li, W. G. and T. L. Xu (2011). "ASIC3 channels in multimodal sensory perception." ACS Chem Neurosci 2(1): 26-37.
63. Dussor, G. (2015). "ASICs as therapeutic targets for migraine." Neuropharmacology 94: 64-71.
64 Morenilla-Palao, C., E. Luis, C. Fernandez-Pena, E. Quintero, J. L. Weaver, D. A. Bayliss and F. Viana (2014). "Ion channel profile of TRPM8 cold receptors reveals a role of TASK-3 potassium channels in thermosensation." Cell Rep 8(5): 1571-1582.
65. Browne, L. E., J. P. Nunes, J. A. Sim, V. Chudasama, L. Bragg, S. Caddick and R. A. North (2014). "Optical control of trimeric P2X receptors and acid-sensing ion channels." Proc Natl Acad Sci USA 111(1): 521-526.
66. Immke, D. C. and E. W. McCleskey (2001). "Lactate enhances the acid-sensing Na+ channel on ischemia-sensing neurons." Nat Neurosci 4(9): 869-870.
67. Rannou, F., R. Leschiera, M. A. Giroux-Metges and J. P. Pennec (2012). "Effects of lactate on the voltage-gated sodium channels of rat skeletal muscle: modulating current opinion." J Appl Physiol (1985) 112(9): 1454-1465.
68. Samuvel, D. J., K. P. Sundararaj, A. Nareika, M. F. Lopes-Virella and Y. Huang (2009). "Lactate boosts TLR4 signaling and NF-kappaB pathway-mediated gene transcription in macrophages via monocarboxylate transporters and MD-2 up-regulation." J Immunol 182(4): 2476-2484.
69. Scalise, M. et al. The Human SLC1A5 (ASCT2) Amino Acid Transporter: From Function to Structure and Role in Cell Biology. Cell Dev Biol. 2018; 6:96, pp. 1-17.
70. Scalise M., Pochini L., Galluccio M., Console L., Indiveri C. (2017). Glutamine transport and mitochondrial metabolism in cancer cell growth. Front. Oncol. 7:306.
71. Kanai Y., Clémençon B., Simonin A., Leuenberger M., Lochner M., Weisstanner M., et al. (2013). The SLC1 high-affinity glutamate and neutral amino acid transporter family. Mol. Aspects Med. 34, 108-120.
72. Poffenberger M. C., Jones R. G. (2014). Amino acids fuel T cell-mediated inflammation. Immunity 40, 635-637.
73. Zheng, H., W. H. Xiao and G. J. Bennett (2012). "Mitotoxicity and bortezomib-induced chronic painful peripheral neuropathy." Exp Neurol 238(2): 225-234.
74 Bender, D. A. (2012). Amino acid metabolism. Chichester, West Sussex, Wiley-Blackwell.
75. Divakaruni, A. S., A. Paradyse, D. A. Ferrick, A. N. Murphy and M. Jastroch (2014). "Analysis and interpretation of microplate-based oxygen consumption and pH data." Methods Enzymol 547: 309-354.
76. Yang, C., L. Jiang, H. Zhang, L. A. Shimoda, R. J. DeBerardinis and G. L. Semenza (2014). "Analysis of hypoxia-induced metabolic reprogramming." Methods Enzymol 542: 425-455.
77. Tominaga, M., M. J. Caterina, A. B. Malmberg, T. A. Rosen, H. Gilbert, K. Skinner, B. E. Raumann, A. I. Basbaum and D. Julius (1998). "The cloned capsaicin receptor integrates multiple pain-producing stimuli." Neuron 21(3): 531-543.

What is claimed is:

1. A method of alleviating pain in a subject, comprising administering a therapeutically effective amount of ASCT2-targeted translation enhancing RNA (teRNA) to a subject in need thereof,
   wherein the ASCT2-targeted teRNA is a RNA molecule that binds with specificity to ASCT2 mRNA uORF and interferes with ribosomal interaction with the ASCT2 mRNA uORF, and
   wherein the RNA molecule ranges in size from about 10 to 40 nucleotides in length.

2. A method of prophylactically blocking pain in a subject, comprising administering a therapeutically effective amount of ASCT2-targeted teRNA to a subject in need thereof,
   wherein the ASCT2-targeted teRNA is a RNA molecule that binds with specificity to ASCT2 mRNA uORF and interferes with ribosomal interaction with the ASCT2 mRNA uORF, and
   wherein the RNA molecule ranges in size from about 10 to 40 nucleotides in length.

3. The method of claim 1, wherein the ASCT2-targeted teRNA is one or more teRNAs selected from the group consisting of: 5'-CAUGCCUCAGCCCGGCAGGG-3' (SEQ ID NO:4); 5'-CAUGCCUCAGCCCGGCAG-3' (SEQ ID NO:5); 5'-CAUGCCUCAGCCCGGC-3' (SEQ ID NO:6); 5'-CAUUGUCUGAGAGGCUGGGU-3' (SEQ ID NO:7); 5'-CAUUGUCUGAGAGGCUGG-3' (SEQ ID NO:8); 5'-CAUUGUCUGAGAGGCU-3' (SEQ ID NO:9); 5'-CAUUGUGGGUUCGGGGUGAG-3' (SEQ ID NO:10); 5'-CAUUGUGGGUUCGGGGUG-3' (SEQ ID NO:11); 5'-CAUUGUGGGUUCGGGG-3' (SEQ ID NO:12); 5'-CAUGCAGCAAACUUAAUACC-3' (SEQ ID NO:13); 5'-CAUGCAGCAAACUUAAUA-3' (SEQ ID NO:14); 5'-CAUGCAGCAAACUUAA-3' (SEQ ID NO:15); 5'-CAUUGUCUGAGAGGCUGGGU-3' (SEQ ID NO:16); 5'-CAUUGUCUGAGAGGCUGG-3' (SEQ ID NO:17); 5'-CAUUGUCUGAGAGGCU-3' (SEQ ID NO:18); 5'-CAUGCCUCAGCCCGGCAGGG-3' (SEQ ID NO:19); 5'-CAUGCCUCAGCCCGGCAG-3' (SEQ ID NO:20); 5'-CAUGCCUCAGCCCGGC-3' (SEQ ID NO:21); 5'-CAUUGUGGGUUCGGGGUGAG-3' (SEQ ID NO:22); 5'-CAUUGUGGGUUCGGGGUG-3' (SEQ ID NO:23); 5'-CAUUGUGGGUUCGGGG-3' (SEQ ID NO:24); 5'-CAUGGAGAAACCCCAUCUCU-3' (SEQ ID NO:25); 5'-CAUGGAGAAACCCCAUCU-3' (SEQ ID NO:26); 5'-CAUGGAGAAACCCCAU-3' (SEQ ID NO:27); 5'-CAUUUGUGUUUUGAAAAGAU-3' (SEQ ID NO:28); 5'-CAUUUGUGUUUUGAAAAG-3' (SEQ ID NO:29); 5'-CAUUUGUGUUUUGAAA-3' (SEQ ID NO:30); 5'-CAUGGCAGGGCUCUGGGUAC-3' (SEQ ID NO:31); 5'-CAUGGCAGGGCUCUGGGU-3' (SEQ ID NO:32); 5'-CAUGGCAGGGCUCUGG-3' (SEQ ID NO:33); 5'-CAUAGACUGUAGCAAGGAGA-3' (SEQ ID NO:34); 5'-CAUAGACUGUAGCAAGGA-3' (SEQ ID NO:35); 5'-CAUAGACUGUAGCAAG-3' (SEQ ID NO:36); 5'-CAUAAUCUACUGUGGCUAGA-3' (SEQ ID NO:37); 5'-CAUAAUCUACUGUGGCUA-3' (SEQ ID NO:38); 5'-CAUAAUCUACUGUGGC-3' (SEQ ID NO:39); 5'-CAUUCAAAGAAGAGCCAUAA-3' (SEQ ID NO:40); 5'-CAUUCAAAGAAGAGCCAU-3' (SEQ ID NO:41); 5'-CAUUCAAAGAAGAGCC-3' (SEQ ID NO:42); 5'-CAUCUGAGCUGAGACCUGGA-3' (SEQ ID NO:43); 5'-CAUCUGAGCUGAGACCUG-3' (SEQ ID NO:44); 5'-CAUCUGAGCUGAGACC-3' (SEQ ID NO:45).

4. The method of claim 1, wherein the ASCT2-targeted teRNA is one or more sequence variants of the teRNAs set forth in SEQ ID NOs:4-45 having at least 90% sequence identity over their entire length to a teRNAs set forth in one of SEQ ID NOs:4-45 and having the same activity as the teRNA upon which they are based.

5. The method of claim 3, wherein the ASCT2-targeted teRNA contains one or more of the following chemical modifications and/or nucleotide analogs: phosphodiester backbone; phosphorothioate backbone; 2-aminopurine; 2,6-diaminopurine; 5-bromo-deoxyuridine; deoxyuridine;

inverted dideoxy-T incorporated at the 3'- and/or 5'-end; 5-methyl deoxycytidine; deoxyInosine; super T (5-hydroxybutynl-2'-deoxyuridine); super G (8-aza-7-deazaguanosine); locked nucleic acids; 5-nitroindole; 2'-O-methyl RNA; hydroxymethyl dC; iso-dC; iso-dG; fluoro C, U, A or G; one or more 2'-O-methoxy-ethyl bases.

6. The method of claim 1, wherein the ASCT2-targeted teRNA is conjugated with N-acetylgalactosamine (GalNAc) or combined with a lipid or polymer.

7. The method of claim 1, wherein the ASCT2-targeted teRNA is formulated as a pharmaceutical composition comprising one or more ASCT2-targeted teRNA and a pharmaceutically acceptable carrier, diluent or excipient.

8. The method of claim 1, wherein the therapeutically effective amount of ASCT2-targeted teRNA is administered to the subject intrathecally.

9. The method of claim 8, wherein the intrathecal administration is direct administration to trigeminal and/or dorsal root ganglia.

10. The method of claim 1, wherein the subject is experiencing acute pain or chronic pain.

11. The method of claim 1, wherein the pain is one or more of the following types of pain and/or pain associated with one or more of the following conditions or diseases: cancer pain, CIPN, AIDS-related pain, ankylosing spondylitis, arachnoiditis, arthritis, arthrofibrosis, ataxic cerebral palsy, autoimmune atrophic gastritis, autoimmune diseases, avascular necrosis, back pain, breakthrough pain, burning mouth syndrome, bursitis, CARDASIL syndrome, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pancreatitis, coccyx, collapsed lung (pneumothorax), complex regional pain syndrome, corneal neuropathic pain, Crohn's disease, degenerative disc disease, Dercum's disease, dermatomyositis, diabetic peripheral neuropathy, dystonia, Rhlers-Danlos syndrome, endometriosis, eosinophilia-myalgia syndrome, erythromelalgia, failed back surgery syndrome, fibromyalgia, gout, headaches, herniated disc, hydrocephalus, intercostal neuraligia, interstitial cystitis, irritable bowel syndrome, juvenile dermatositis, loin pain-haematuria syndrome, lupus, lyme disease, medullary sponge kidney, meralgia paresthetica, mesothelioma, migraine, mitochondrial disorders, multiple sclerosis, musculoskeletal pain, myofascial pain, myositis, neuropathic pain, occipital neuralgia, osteoarthritis, Paget's disease, parsonage turner syndrome, pelvic pain, peripheral neuropathy, phantom limb pain, pinched nerve, polycystic kidney disease, polymyalgia rhuematica, polymyositis, porphyria, post-herniorraphy pain syndrome, post-mastectomy pain syndrome, post-stroke pain, post-thorocotomy pain syndrome, post-herpetic neuralgia (shingles), post-polio syndrome, primary lateral sclerosis, psoriatic arthritis, pudendal neuralgia, radiculopathy, Raynaud's disease, rheumatoid arthritis, sacroiliac joint dysfunction, sarcoidosis, Scheuemann's kyphosis disease, sciatica, scoliosis, sickle cell, Sjogren's syndrome, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, temporomandibular joint disorder, transverse myelitis, trigeminal neuralgia, ulcerative colitis, vascular pain, vulvodynia and whiplash.

12. The method of claim 2, wherein the subject is expecting to experience acute pain or chronic pain.

13. The method of claim 12, wherein the pain is one or more of the following types of pain and/or pain associated with one or more of the following conditions or diseases: cancer pain, CIPN, AIDS-related pain, ankylosing spondylitis, arachnoiditis, arthritis, arthrofibrosis, ataxic cerebral palsy, autoimmune atrophic gastritis, autoimmune diseases, avascular necrosis, back pain, breakthrough pain, burning mouth syndrome, bursitis, CARDASIL syndrome, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pancreatitis, coccyx, collapsed lung (pneumothorax), complex regional pain syndrome, corneal neuropathic pain, Crohn's disease, degenerative disc disease, Dercum's disease, dermatomyositis, diabetic peripheral neuropathy, dystonia, Rhlers-Danlos syndrome, endometriosis, eosinophilia-myalgia syndrome, erythromelalgia, failed back surgery syndrome, fibromyalgia, gout, headaches, herniated disc, hydrocephalus, intercostal neuraligia, interstitial cystitis, irritable bowel syndrome, juvenile dermatositis, loin pain-haematuria syndrome, lupus, lyme disease, medullary sponge kidney, meralgia paresthetica, mesothelioma, migraine, mitochondrial disorders, multiple sclerosis, musculoskeletal pain, myofascial pain, myositis, neuropathic pain, occipital neuralgia, osteoarthritis, Paget's disease, parsonage turner syndrome, pelvic pain, peripheral neuropathy, phantom limb pain, pinched nerve, polycystic kidney disease, polymyalgia rhuematica, polymyositis, porphyria, post-herniorraphy pain syndrome, post-mastectomy pain syndrome, post-stroke pain, post-thorocotomy pain syndrome, post-herpetic neuralgia (shingles), post-polio syndrome, primary lateral sclerosis, psoriatic arthritis, pudendal neuralgia, radiculopathy, Raynaud's disease, rheumatoid arthritis, sacroiliac joint dysfunction, sarcoidosis, Scheuemann's kyphosis disease, sciatica, scoliosis, sickle cell, Sjogren's syndrome, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, temporomandibular joint disorder, transverse myelitis, trigeminal neuralgia, ulcerative colitis, vascular pain, vulvodynia and whiplash.

14. The method of claim 1, further comprise administering one or more therapeutically effective agent to the subject, wherein the therapeutically effective agent is one that counteracts a metabolic change in a sensory neuron.

15. The method of claim 14, wherein the therapeutically effective agent is one or more of dichloroacetate (DCA), oxamate and 2-deoxy-d-glucose (2DG).

16. The method of claim 14, wherein the ASCT2-targeted teRNA and the therapeutically effective agent are administered sequentially, in either order.

17. The method of claim 14, wherein the ASCT2-targeted teRNA and the therapeutically effective agent are administered concurrently.

* * * * *

SEQUENCE LISTING

<160> NUMBER OF SEQ ID NOS: 47

<210> SEQ ID NO 1
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 1
cauagauccg ggaugccuug                                                   20

<210> SEQ ID NO 2
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 2
cauagauccg ggaugccu                                                     18

<210> SEQ ID NO 3
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 3

```
cauagauccg ggaugc                                              16
```

<210> SEQ ID NO 4
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 4

```
caugccucag cccggcaggg                                          20
```

<210> SEQ ID NO 5
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 5

```
caugccucag cccggcag                                            18
```

<210> SEQ ID NO 6
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 6

```
caugccucag cccggc                                              16
```

<210> SEQ ID NO 7
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 7

```
cauugucuga gaggcugggu                                          20
```

<210> SEQ ID NO 8
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 8

```
cauugucuga gaggcugg                                            18
```

<210> SEQ ID NO 9
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 9
cauugucuga gaggcu                                                16

<210> SEQ ID NO 10
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 10
cauugugggu ucggggugag                                            20

<210> SEQ ID NO 11
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 11
cauugugggu ucggggug                                              18

<210> SEQ ID NO 12
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 12
cauugugggu ucgggg                                                16

<210> SEQ ID NO 13
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 13
caugcagcaa acuuaauacc                                            20

<210> SEQ ID NO 14
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 14
caugcagcaa acuuaaua                                              18

<210> SEQ ID NO 15
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 15
caugcagcaa acuuaa                                                16

```
<210> SEQ ID NO 16
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 16
cauugucuga gaggcugggu                                                      20

<210> SEQ ID NO 17
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 17
cauugucuga gaggcugg                                                        18

<210> SEQ ID NO 18
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 18
cauugucuga gaggcu                                                          16

<210> SEQ ID NO 19
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 19
caugccucag cccggcaggg                                                      20

<210> SEQ ID NO 20
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 20
caugccucag cccggcag                                                        18

<210> SEQ ID NO 21
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 21
caugccucag cccggc                                                          16
```

```
<210> SEQ ID NO 22
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 22 cauuguggguu ucgggguagag                                              20

<210> SEQ ID NO 23
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 23
cauugugggu ucgggguag                                                 18

<210> SEQ ID NO 24
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 24
cauugugggu ucgggg                                                    16

<210> SEQ ID NO 25
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 25
cauggagaaa ccccaucucu                                                20

<210> SEQ ID NO 26
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 26
cauggagaaa ccccaucu                                                  18

<210> SEQ ID NO 27
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 27
cauggagaaa ccccau                                                    16
```

```
<210> SEQ ID NO 28
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 28
cauuuguguu uugaaaagau                                              20

<210> SEQ ID NO 29
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 29
cauuuguguu uugaaaag                                                18

<210> SEQ ID NO 30
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 30
cauuuguguu uugaaa                                                  16

<210> SEQ ID NO 31
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 31
cauggcaggg cucuggguac                                              20

<210> SEQ ID NO 32
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 32
cauggcaggg cucugggu                                                18

<210> SEQ ID NO 33
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 33
cauggcaggg cucugg                                                  16

<210> SEQ ID NO 34
```

```
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 34
cauagacugu agcaaggaga                                                 20

<210> SEQ ID NO 35
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 35
cauagacugu agcaagga                                                   18

<210> SEQ ID NO 36
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 36
cauagacugu agcaag                                                     16

<210> SEQ ID NO 37
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 37
cauaaucuac uguggcuaga                                                 20

<210> SEQ ID NO 38
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 38
cauaaucuac uguggcua                                                   18

<210> SEQ ID NO 39
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 39
cauaaucuac uguggc                                                     16

<210> SEQ ID NO 40
<211> LENGTH: 20
```

```
<212> TYPE: RNA
<213> ORGANISM: Artificial Sequence
<220> FEATURE:
<223> OTHER INFORMATION: chemically-synthesized translation enhancing
      RNA

<400> SEQUENCE: 40
cauucaaaga agagccauaa                                              20

<210> SEQ ID NO 41
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 41
cauucaaaga agagccau                                                18

<210> SEQ ID NO 42
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 42
cauucaaaga agagcc                                                  16

<210> SEQ ID NO 43
<211> LENGTH: 20
<212> TYPE: RNA
<213> ORGANISM: Artificial Sequence
<220> FEATURE:
<223> OTHER INFORMATION: chemically-synthesized translation enhancing
      RNA

<400> SEQUENCE: 43
caucugagcu gagaccugga                                              20

<210> SEQ ID NO 44
<211> LENGTH: 18
<212> TYPE: RNA
<213> ORGANISM: Artificial Sequence
<220> FEATURE:
<223> OTHER INFORMATION: chemically-synthesized translation enhancing
      RNA

<400> SEQUENCE: 44
caucugagcu gagaccug                                                18

<210> SEQ ID NO 45
<211> LENGTH: 16
<212> TYPE: RNA
<213> ORGANISM: Artificial Sequence
<220> FEATURE:
<223> OTHER INFORMATION: chemically-synthesized translation enhancing
      RNA

<400> SEQUENCE: 45
caucugagcu gagacc                                                  16

<210> SEQ ID NO 46
<211> LENGTH: 16
<212> TYPE: RNA
```

```
<213> ORGANISM: Artificial Sequence
<220> FEATURE:
<223> OTHER INFORMATION: chemically-synthesized translation enhancing
      RNA

<400> SEQUENCE: 46
cauacuacgc cguagc                                                      16

<210> SEQ ID NO 47
<211> LENGTH: 400
<212> TYPE: DNA
<213> ORGANISM: Mus musculus

<400> SEQUENCE: 47
gatctcggtc tcccggagca aggcatcccg gatctatgcc acttgggttg agcttcctga      60
agacctcagc tacctgagtt tccttactcc ttcagggagt caaagaaccc tctgaagagc     120
tgttccctac tccaacaagg cgctctcaac tcccagtttt cggggattcg acatcaccag     180
gaaaaataaa gggatctccg catacagctc agggagccta ggaccctcca gtttccgaga     240
tccggtggac gcataacttc aaggaccgct gcaaagtttc agcctccatt ctcggtccta     300
aggacgtcac acctagtctc caggctcaca aggaacctcc ctgttacggc tcagcatggc     360
agtggatccc cctaaggctg accccaaagg ggtagtagcg                           400
```